(12) United States Patent
Xiao et al.

(10) Patent No.: US 11,690,874 B2
(45) Date of Patent: Jul. 4, 2023

(54) USE OF CHIMERIC ANTIGEN RECEPTOR MODIFIED CELLS TO TREAT AUTOIMMUNE DISEASE

(71) Applicants: Innovative Cellular Therapeutics Holdings, Ltd., George Town (KY); Zhejiang University, Zhejiang Sheng (CN)

(72) Inventors: Lei Xiao, Shanghai (CN); Chengfei Pu, Shanghai (CN); Zhao Wu, Shanghai (CN); Linrong Lu, Shanghai (CN)

(73) Assignees: Innovative Cellular Therapeutics Holdings, Ltd., George Town (KY); Zhejiang University, Zhejiang Sheng (CN)

( * ) Notice: Subject to any disclaimer, the term of this patent is extended or adjusted under 35 U.S.C. 154(b) by 389 days.

(21) Appl. No.: 16/568,799

(22) Filed: Sep. 12, 2019

(65) Prior Publication Data

US 2020/0078403 A1    Mar. 12, 2020

Related U.S. Application Data

(60) Provisional application No. 62/775,143, filed on Dec. 4, 2018, provisional application No. 62/730,225, filed on Sep. 12, 2018.

(51) Int. Cl.
*A61K 35/17* (2015.01)
*C07K 16/28* (2006.01)
*A61K 38/00* (2006.01)

(52) U.S. Cl.
CPC .......... *A61K 35/17* (2013.01); *C07K 16/2803* (2013.01); *A61K 38/00* (2013.01)

(58) Field of Classification Search
CPC .. A61K 35/17; C07K 2317/622; C07K 14/28; A61P 35/00
See application file for complete search history.

(56) References Cited

U.S. PATENT DOCUMENTS

2010/0104509 A1 *  4/2010  King ................. C07K 16/2803
424/1.49

FOREIGN PATENT DOCUMENTS

WO   WO-2017046747 A1 *  3/2017   ......... A61K 31/4985
WO   WO-2017177137 A1 * 10/2017   ......... C07K 16/2896

OTHER PUBLICATIONS

La Paglia et al. 2017; One year in review 2017: systemic lupus erythematosus. Clin. Exp. Rheumatol. 35: 551-561.*
Alabanza et al. 2017: Function of notvel anti-CD19 chimeric antigen receptors with human variable regions is affected by the hinge and transmembrane domains. Molecular Therapy. 25(11): 2452-2465.*

* cited by examiner

*Primary Examiner* — Karen Cochrane Carlson
(74) *Attorney, Agent, or Firm* — Lee & Hayes, P.C.

(57) ABSTRACT

Embodiments of the present disclosure include a method for treating Systemic Lupus Erythematosus (SLE) using CD19 CAR T cells. The method includes administering to the human patient a pharmaceutically effective amount of a population of T cells of the human patient that express a chimeric antigen receptor (CAR) that comprises the amino acid sequence of, e.g., SEQ ID NO: 23.

11 Claims, 13 Drawing Sheets
Specification includes a Sequence Listing.

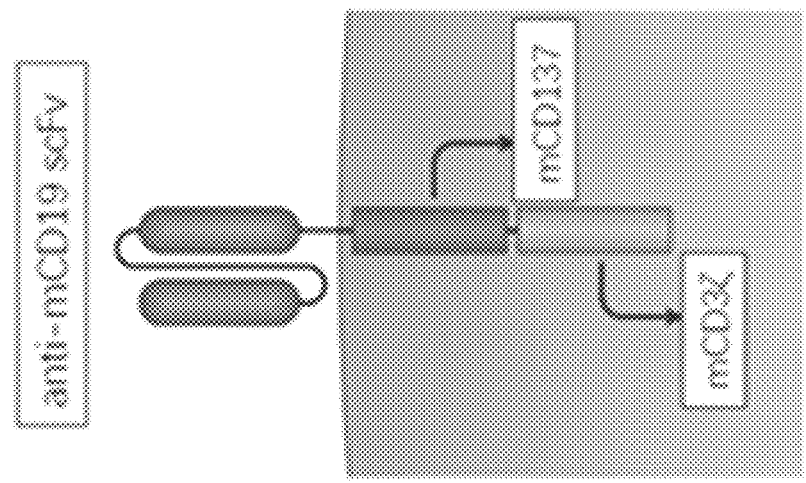
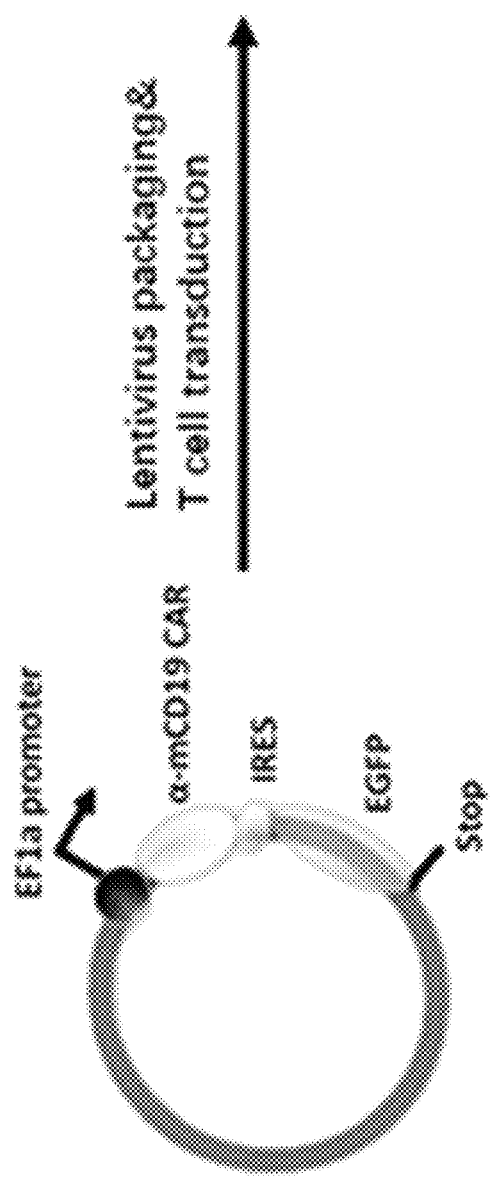
FIG. 4

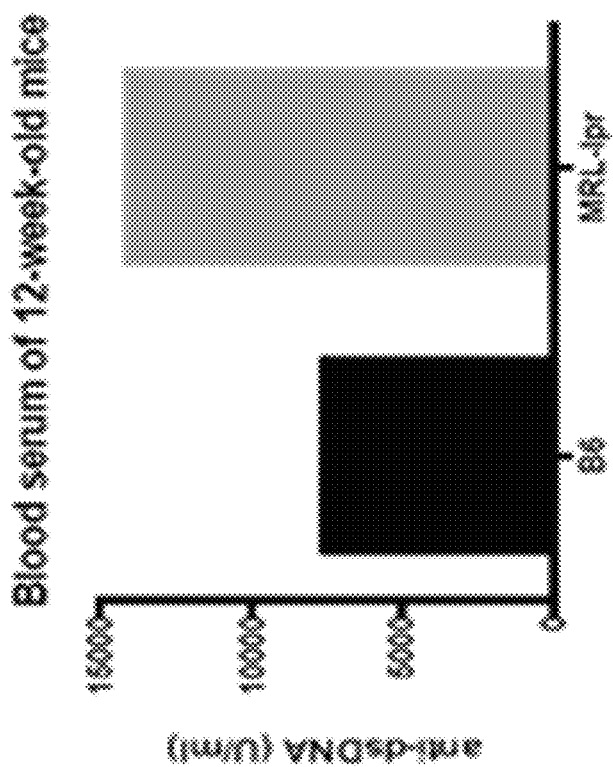
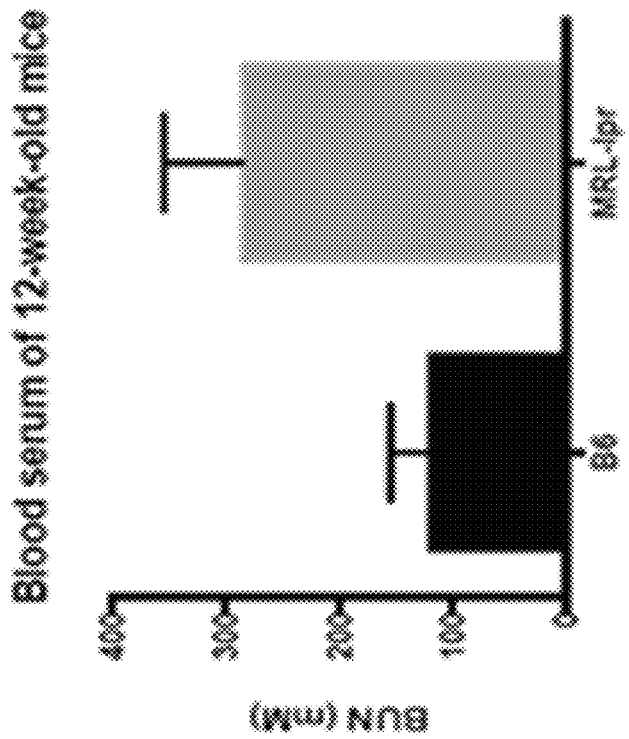
FIG. 8

FIG. 10
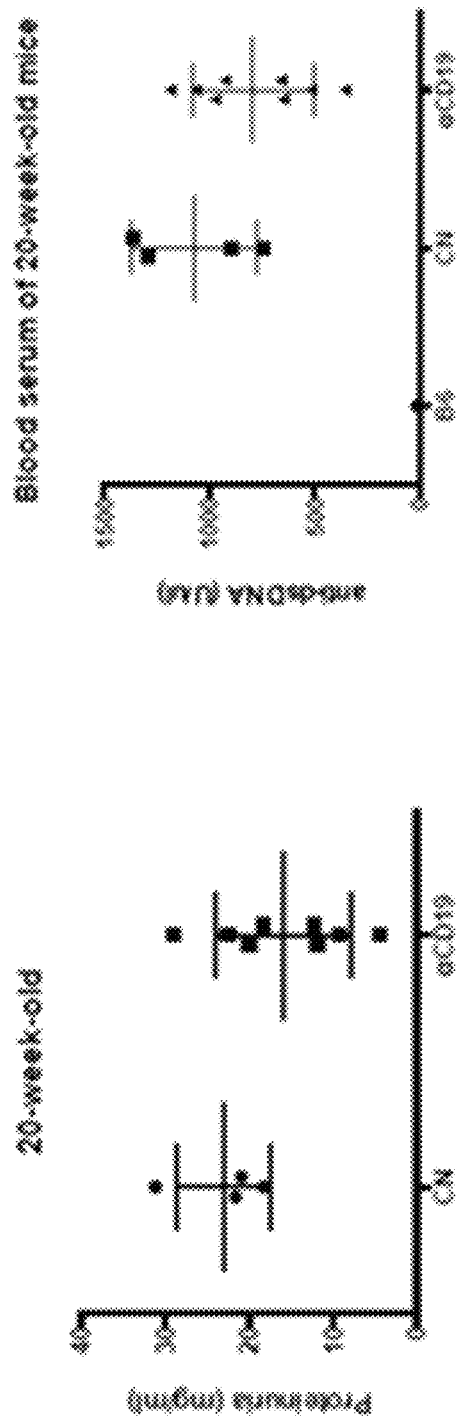
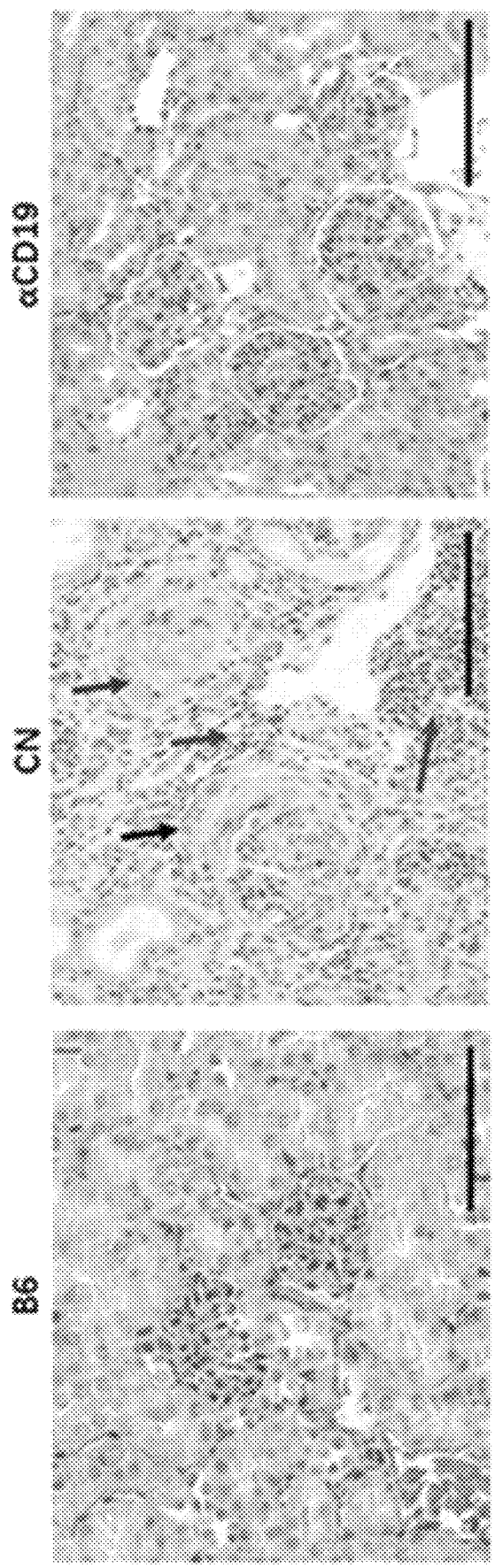

USE OF CHIMERIC ANTIGEN RECEPTOR MODIFIED CELLS TO TREAT AUTOIMMUNE DISEASE

CROSS REFERENCE TO RELATED APPLICATIONS

This application claims the benefit of U.S. Provisional Patent Application 62/730,225 filed on Sep. 12, 2018; and U.S. Provisional Patent Application 62/775,143, filed on Dec. 4, 2018; which are hereby incorporated by reference in their entirety.

SEQUENCE LISTING INFORMATION

A computer readable textfile, entitled "SDS1.0033US_ST25.txt," created on or about Feb. 22, 2022, with a file size of about 34 KB, contains the sequence listing for this application and is hereby incorporated by reference in its entirety.

TECHNICAL FIELD

The present disclosure relates to modified cells and users, in particular to compositions and methods for treating autoimmune disease using chimeric antigen receptor modified cells.

BACKGROUND

Systemic autoimmune diseases can be life-threatening, in which, the 10-year survival rates of Systemic Lupus Erythematosus (SLE) is 89%. Patients with Multiple Sclerosis (MS) have shortened the life expectancy of 7 to 14 years compared to the normal population. Furthermore, the quality of life is generally compromised not only from disease symptoms and flares but also from routine avoidance of environmental triggers.

Therapeutic measures for these diseases are usually supportive treatment due to their incurable nature. Conventionally, systemic administration of immunosuppressant is used to manage disease severity and decrease relapse rate, but the long-term use of immune suppressive drugs can result in various side effects, including fatigue, allergies, shingles, kidney problems, and heart problems.

Recently, B lymphocyte depleting therapy has shown to effectively suppress SLE and MS activity measures, including the development of new enhancing lesions and relapse rates. Unlike conventional systemic immunosuppressive drugs, which may excessively down-regulate a vast array of immune activities, monoclonal antibodies targeting CD19, CD20, B cell maturation antigen (BCMA), or BAFF-R specifically deplete B lymphocyte-mediated immune responses, therefore minimizing possible side effects of systemic immunosuppression.

However, the therapeutic regime using monoclonal antibodies usually requires weekly IV administration over the course of one month, and the average half-life after a complete infusion is approximately 21 days (for Rituximab)). The time-to-effect only begins approximately six weeks after the primary infusion, and the full effect usually does not take place until the third month. Moreover, disease symptoms can resurface as soon as nine months post infusion.

SUMMARY

Embodiments relate to treatment of autoimmune disease with T cell therapy. Embodiments include methods and system for the use of chimeric antigen receptor modified cells to treat autoimmune disease. For example, the method includes administering to a subject a pharmaceutically effective amount of a population of T cells of the subject expressing a chimeric antigen receptor (CAR) that binds to an antigen associated with B cells. In embodiments, the autoimmune disease is an autoimmune disease associated with B cell proliferation and immunoglobulin secretion. In embodiments, the autoimmune disease is Systemic Lupus Erythematosus (SLE), Rheumatoid Arthritis (RA), Type 1 Diabetes (T1D), Sjögren's syndrome, or Multiple Sclerosis (MS). In embodiments, the antigen is BAFF, APRIL, CD19, CD20, CD22, a B cell receptor (BCR), BCMA, or CD79.

In embodiments, the antigen is CD19, CD20, or BAFF. In embodiments, the pharmaceutically effective amount of a population of T cells is about $10^4$ to $10^9$ cells per kg body weight of the human patient. In embodiments, the pharmaceutically effective amount of a population of T cells is about $10^5$ to $10^6$ cells per kg body weight of the human patient. In embodiments, the pharmaceutically effective amount of a population of T cells is about $10^6$ to $10^7$ cells per kg body weight of the human patient. In embodiments, the pharmaceutically effective amount of a population of T cells is about $10^4$ to $10^5$ cells per kg body weight of the human patient. In embodiments, the pharmaceutically effective amount of a population of T cells is about $10^7$ to $10^8$ cells per kg body weight of the human patient. In embodiments, the pharmaceutically effective amount of a population of T cells is about $10^8$ to $10^9$ cells per kg body weight of the human patient.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIG. 4 shows preparation of anti-mouse CD19 CAR-T cells.

FIG. 8 shows serum characterization of 12-week-old SLE disease model mice and normal B6 mice.

FIG. 10 shows the renal function damage of the SLE disease model mice after treatment in the control group and the experimental group.

DETAILED DESCRIPTION

Figure 1:
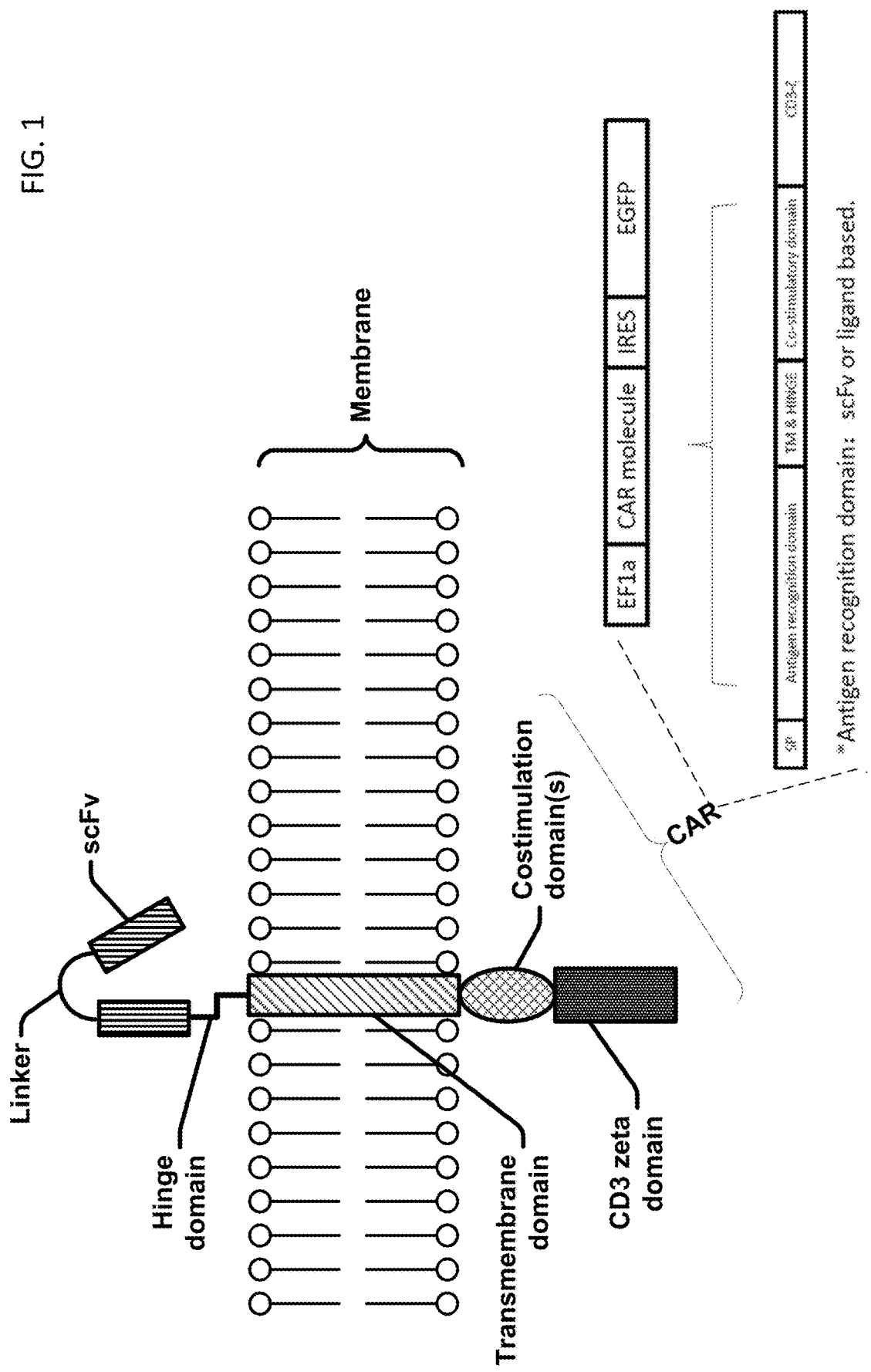
FIG. 1 a schematic diagram illustrating CAR structure.

Systemic lupus erythematosus (SLE) is an autoimmune disease involving multiple organs. It occurs mostly in people aged 14-44 years, and the incidence in women is about 10 times that of men. The etiology of SLE has not yet been determined. Studies have shown that B cells in SLE patients proliferate abnormally, produce a large number of autoantibodies that bind to the corresponding autoantigens in the body, directly destroy the cells, or cause acute and chronic inflammation and tissue necrosis under the effect of complement, which lead to multiple system damage in the body. At present, treatments for SLE mainly include replacement of plasma, injection of immunoglobulin, injection of monoclonal antibodies against B cells, and the like. With the presence of a B cell surface characteristic antigen, anti-CD19 chimeric antigen receptor T cells (anti-CD19 CAR-T cells) can specifically kill B cells, which can provide a new strategy for the treatment of SLE. To validate the therapeutic effect of anti-CD19 CAR-T cells on SLE, Applicants performed experiments in SLE disease model mice.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

Unless otherwise indicated, all numbers expressing quantities used throughout the specification and claims are to be understood as being modified in all instances by the term "about." At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of +1% to ±20% of the stated value.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. κ and λ light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an antigen mistakenly recognized by the immune system as being foreign. Autoantigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated or recipient subject, but the donor subject has immune system markers which are similar to the recipient subject.

The term "xenogeneic" is used to describe a graft derived from an subject of a different species. As an example, the donor subject is from a different species than a recipient subject and the donor subject and the recipient subject can be genetically and immunologically incompatible.

The term "cancer" as used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any elements listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially frr from components that normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence.

For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "parenteral administration" of a composition includes, e.g., subcutaneous (s.c.), intravenous (i.v.), intramuscular (i.m.), intrastemal injection, or infusion techniques.

The terms "patient," "subject," and "individual," and the like are used interchangeably herein, and refer to any human, animal, or living organism, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals such as dogs, cats, mice, rats, and transgenic species thereof.

A subject in need of a treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynudeotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynudeotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a particular second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Further, a Zinc finger binding domain may be fused a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes), as illustrated in FIG. 1.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease. Exemplary target sites for various targeted ZFPs are shown in Table 1.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.5 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures. CD3 zeta is not the only suitable primary signaling domain for a CAR construct with respect to the primary response. For example, back in 1993, both CD3 zeta and FcR gamma were known as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T-cell receptors" PNAS, 1993 Jan. 15; 90(2):720-4, showed that two CAR constructs in which an scFv was fused to "either the FcR y chain or the CD3 complex s chain" triggered T cell activation and target cell. Notably, as demonstrated in Eshhar et al., CAR constructs containing only the primary signaling domain CD3 zeta or FcR gamma are functional without the co-presence of co-stimulatory domains. Additional non-CD3 zeta based CAR constructs have been developed over the years. For example, Wang et al., "A Chimeric Antigen Receptor (CARs) Based Upon a Killer Immunoglobulin-Like Receptor (KIR) Triggers Robust Cytotoxic Activity in Solid Tumors" Molecular Therapy, vol. 22, no. Suppl.1, May 2014, page S57, tested a CAR molecule in which an scFv was fused to "the transmembrane and cytoplasmic domain of a killer immunoglobulin-like receptor (KIR). Wang et al. reported that, "a KIR-based CAR targeting mesothelin (SS 1-KIR) triggers antigen-specific cytotoxic activity and cytokine production that is comparable to CD3~-based CARs." A second publication from the same group, Wang et al., "Generation of Potent T-cell Immunotherapy for Cancer Using DAP12-Based, Multichain, Chimeric Immunoreceptors" Cancer Immunol Res. 2015 July; 3(7):815-26, showed that a CAR molecule in which "a single-chain variable fragment for antigen recognition [was fused] to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen presenting cell (e.g., an APC, a dendritic cell, a B cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate transfer of nucleic acid into cells, such as, for example, polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present disclosure relates to the discovery of the use of CAR-T cells that identify malignant B cells to deplete malignant B cells. In contrast to conventional treatments, CAR-T therapy uses genetically engineered autologous T lymphocyte to target and destroy "marker-expressing" cells. CAR-T not only possess the target specificity of monoclonal antibody treatment, but it could also provide long-lasting therapeutic effect due to its' capacity to convert into memory T lymphocyte.

Unlike conventional therapies, the present disclosure describes treating B lymphocyte-associated autoimmune disease using CAR-T technology targeting markers such as CD19, CD20, and BAFF-R. Embodiments herein uses lentivirus-engineered autologous T lymphocytes that express and display antibody that targets B lymphocyte-specific marker, at the same time retaining the otherwise "healthy" immune system.

As compared to the conventional therapies, the embodiments described herein provide longer-lasting therapeutic effect, which benefits subjects by avoiding routine medication and prolonged usage of potentially cytotoxic drugs. Further, the embodiments described herein provide faster-acting therapeutic effect than the monoclonal antibody treatment.

Embodiments relate to treatment using T cell therapy. The embodiments described herein include methods and system for using chimeric antigen receptor modified cells to treat autoimmune diseases. For example, the method includes administering to a human patient a pharmaceutically effective amount of a population of T cells of the human patient that express a chimeric antigen receptor (CAR) that binds to an antigen associated with B cells.

Modified T cells may be derived from a stem cell. The stem cells may be adult stem cells, embryonic stem cells, more particularly non-human stem cells, cord blood stem cells, progenitor cells, bone marrow stem cells, induced pluripotent stem cells, totipotent stem cells or hematopoietic stem cells. A modified cell may also be a dendritic cell, a NK-cell, a B cell or a T cell selected from the group consisting of inflammatory T lymphocytes, cytotoxic T lymphocytes, regulatory T lymphocytes or helper T lymphocytes. In embodiments, Modified cells may be derived from the group consisting of CD4+T lymphocytes and CD8+T lymphocytes. Prior to expansion and genetic modification of the cells of the invention, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art, may be used. In embodiments, modified cells may be derived from a healthy donor, from a subject diagnosed with cancer or from a subject diagnosed with an infection. In embodiments, modified cell is part of a mixed population of cells which present different phenotypic characteristics.

The term "stem cell" refers to any of certain types of cell which have the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cell may be distinguished on the basis of their origin and/or on the extent of their capacity for differentiation into other types of cell. For example, stem cell may include embryonic stem (ES) cells (i.e., pluripotent stem cells), somatic stem cells, Induced pluripotent stem cells, and any other types stem cells.

The pluripotent embryonic stem cells may be found in the inner cell mass of a blastocyst and have high innate capacity for differentiation. For example, pluripotent embryonic stem cells may have the potential to form any type of cell in the body. When grown in vitro for long periods of time, ES cells maintain pluripotency: progeny cells retain the potential for multilineage differentiation. Somatic stem cells may include the fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited range of types of cell and have been described as multipotent. The 'tissue-specific' stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing a expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells may be made from adult stomach, liver, skin cells and blood cells.

In embodiments, the polynucleotide may integrate into the genome of the modified cell and descendants of the modified cell will also express the polynucleotide, resulting in a stably transfected modified cell. In embodiments, the modified cell may express the polynucleotide encoding the CAR but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

Viruses can be used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

There also exist non-viral methods for delivering nucleic acids into a cell, for example, electroporation, gene gun, sonoporation, magnetofection, and the use of oligonucleotides, lipoplexes, dendrimers, and inorganic nanoparticles.

In embodiments, the autoimmune disease is an autoimmune disease associated with B cell proliferation and immunoglobulin secretion. In embodiments, the autoimmune disease is Systemic Lupus Erythematosus (SLE), Rheumatoid Arthritis (RA), Type 1 Diabetes (T1D), Sjögren's syndrome, or Multiple Sclerosis (MS). In embodiments, the antigen is BAFF, APRIL, CD19, CD20, CD22, a B cell receptor (BCR), BCMA, Tall-1, or CD79. In embodiments, the antigen is CD19, CD20, or BAFF.

In embodiments, the pharmaceutically effective amount of a population of T cells is about $10^4$ to $10^9$ cells per kg body weight of the human patient. In embodiments, the pharmaceutically effective amount of a population of T cells is about $10^5$ to $10^6$ cells per kg body weight of the human patient. In embodiments, the pharmaceutically effective amount of a population of T cells is about $10^6$ to $10^7$ cells per kg body weight of the human patient. In embodiments, the pharmaceutically effective amount of a population of T cells is about $10^4$ to $10^5$ cells per kg body weight of the human patient. In embodiments, the pharmaceutically effective amount of a population of T cells is about $10^7$ to $10^8$ cells per kg body weight of the human patient. In embodiments, the pharmaceutically effective amount of a population of T cells is about $10^8$ to $10^9$ cells per kg body weight of the human patient.

Embodiments relate to a method or use of a polynucleotide encoding a CAR binding CD19 to treat the autoimmune disease. The method or use includes: providing a viral particle (e.g., AAV or its variants) comprising a vector genome (CD19 CAR in FIG. 1), the vector genome comprising the polynucleotide, wherein the polynucleotide is operably linked to an expression control element conferring transcription of the polynucleotide (e.g., Hif1a, NFAT, FOXP3, or NFkB); and administering an amount of the viral particle to the subject such that CD19 CAR is expressed in the subject. In embodiments, the AAV preparation may include AAV vector particles, empty capsids and host cell impurities, thereby providing an AAV product substantially free of AAV empty capsids. More information of the administration and preparation of the viral particle may be found at the U.S. Pat. No. 9,840,719, which is incorporated herein by reference.

CARs are molecules generally including an extracellular and intracellular domain. The extracellular domain includes a target-specific binding element. The intracellular domain (e.g., cytoplasmic domain) includes a co-stimulatory signaling region and a zeta chain portion. The co-stimulatory signaling region refers to a portion of the CAR including the intracellular domain of a co-stimulatory molecule. Co-stimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain of the polypeptide chain. A spacer domain may include up to 300 amino acids, preferably 10 to 100 amino acids, and most preferably 25 to 50 amino acids.

In embodiments, the antigen binding element of the CAR of the disclosure targets CD19.

In embodiments, the transmembrane domain of the CAR of the disclosure includes the CD8 or CD9 transmembrane domain. In embodiments, the intracellular domain of the CAR of the disclosure includes the intracellular domain of 4-1BB (CD137) or CD 28.

The embodiments further relate to methods for treating a subject for a disease or condition including administering to the subject an effective amount of the modified cells or a population of modified cells of the present disclosure. Various diseases or conditions can be treated according to the present methods including autoimmune disease. Examples of autoimmune disease include Systemic Lupus Erythematosus (SLE), Rheumatoid Arthritis (RA), Type 1 Diabetes (T1D), Sjögren's syndrome, or Multiple Sclerosis (MS).

In embodiments, the antigen binding molecule is a chimeric antigen receptor (CAR) or a T Cell Receptor (TCR). The term "chimeric antigen receptor" or alternatively a "CAR" refers to a recombinant polypeptide construct comprising at least an extracellular antigen binding domain, a transmembrane domain, and an intracellular signaling domain (e.g., cytoplasmic domain). In embodiments, the domains in the CAR polypeptide construct are on the same polypeptide (e.g., comprising a chimeric fusion protein) or on different polypeptides, i.e. not contiguous with each other.

In embodiments, the intracellular signaling domain may include a functional signaling domain derived from a stimulatory molecule and/or a co-stimulatory molecule as described above. In embodiments, the intracellular signaling domain includes a functional signaling domain derived from a primary signaling domain (e.g., a primary signaling domain of CD3-zeta). In embodiments, the intracellular signaling domain further includes one or more functional signaling domains derived from at least one co-stimulatory molecule. The co-stimulatory signaling region refers to a portion of the CAR including the intracellular domain of a co-stimulatory molecule. Co-stimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may include up to 300 amino acids, 10 to 100 amino acids, or 25 to 50 amino acids.

The extracellular domain of a CAR may include an antigen binding domain (e.g., a scFv, a single domain antibody, or TCR (e.g., a TCR alpha binding domain or TCR beta binding domain)) that targets a specific marker (e.g., CD19). The markers include, for example, CD19, CD22, CD20, BCMA, CD5, CD7, CD2, CD16, CD56, CD30, CD14, CD68, CD11b, CD18, CD169, CD1c, CD33, CD38, CD138, or CD13. For example, when the antigen is CD19, the CAR thereof may be referred as CD19CAR. Sequences of scFv of CD19 CAR and others are provided below and U.S. Pat. No. 6,410,319 (CD20 CAR).

In embodiments, the extracellular ligand-binding domain comprises a scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence $(GGGGS)_3$ (SEQ ID NO: 27), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can, in turn, be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In embodiments, the tumor antigens include CD19, CD22, CD20, BCMA, CD5, CD7, CD2, CD16, CD56, CD30, CD14, CD68, CD11b, CD18, CD169, CD1c, CD33, CD38, CD138, or CD13.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional information related to expression synthetic nucleic acids encoding CARs and gene transfer into mammalian cells is provided in U.S. Pat. No. 8,906,682, incorporated by reference in its entirety.

Pharmaceutical compositions of the present disclosure may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T cells described herein may be administered at a dosage of about $10^4$ to $10^9$ cells/kg body weight, or about $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular subject can readily be determined by one skilled in the art of medicine by monitoring the subject for signs of disease and adjusting the treatment accordingly. In embodiments, it may be desired to administer activated T cells to a subject and then subsequently redraw the blood (or have apheresis performed), collect the activated and expanded T cells, and reinfuse the subject with these activated and expanded T cells. This process can be carried out multiple times every few weeks. In embodiments, T cells can be activated from blood draws of from 10 cc to 400 cc. In embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T cells.

The administration of the pharmaceutical compositions described herein may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous (i. v.) injection, or intraperitoneally. In embodiments, the T cell compositions of the present disclosure are administered to a subject by intradermal or subcutaneous injection. In embodiment, the T cell compositions of the present disclosure are preferably administered by i.v. injection. The compositions of T cells may be injected directly into a tumor, lymph node, or site of infection. In embodiments of the present disclosure, cells activated and expanded using the methods described herein, or other methods known in the art where T cells are expanded to therapeutic levels, are administered to a subject in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS subject or efalizumab treatment for psoriasis subjects or other treatments for PML subjects. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cydosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)).

The dosage of the above treatments to be administered to a subject will vary with the precise nature of the condition being treated and the recipient of the treatment. The scaling of dosages for human administration can be performed according to art-accepted practices by a physician depending on various factors.

Embodiments relate to an in vitro method for preparing modified cells. The method may include obtaining a sample of cells from the subject. For example, the sample may include T cells or T cell progenitors. The method may further include transfecting the cells with a DNA encoding at least a CAR, culturing the population of CAR cells ex vivo in a medium that selectively enhances proliferation of CAR-expressing T cells.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T cells.

In embodiments, the CAR molecules described herein comprise one or more complementarity-determining regions (CDRs) for binding an antigen of interest. CDRs are part of the variable domains in immunoglobulins and T cell receptors for binding a specific antigen. There are three CDRs for each variable domain. Since there is a variable heavy domain and a variable light domain, there are six CDRs for binding an antigen. Further since an antibody has two heavy chains and two light chains, an antibody has twelve CDRs altogether for binding antigens. In embodiments, the CAR molecules comprise one or more CDRs for binding CD19, BAFF, APRIL, CD20, CD22, a B cell receptor (BCR), B cell maturation antigen (BCMA) or CD79.

In embodiments, the population of cells described herein is used in autologous CAR T cell therapy. In embodiments, the CAR T cell therapy is allogenic CAR T cell therapy, TCR T cell therapy, and NK cell therapy.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:
1. A method for treating an autoimmune disease in a human patient, the method comprising: administrating to the human patient a pharmaceutically effective amount of a population of T cells of the human patient that express a chimeric antigen receptor (CAR) that comprising the amino acid sequence of any of SEQ ID NO: 22-24 and 26.

2. A method for treating an autoimmune disease in a human patient, the method comprising: administrating to the human patient a pharmaceutically effective amount of a population of T cells of the human patient that express a chimeric antigen receptor (CAR) that binds an antigen associated with B cells.

3. The method of embodiment 2, wherein the autoimmune disease is an autoimmune disease associated with B cell proliferation and immunoglobulin secretion.

4. The method of embodiment 2, wherein the autoimmune disease is Systemic Lupus Erythematosus (SLE), Rheumatoid Arthritis (RA), Type 1 Diabetes (T1D), Sjögren's syndrome, or Multiple Sclerosis (MS).

5. The method of embodiment 2, wherein the antigen is BAFF, APRIL, CD19, CD20, CD22, a B cell receptor (BCR), B cell maturation antigen (BCMA) or CD79.

6. The method of embodiment 2, wherein the antigen is CD19, CD20 or BAFF.

7. The method of embodiment 2, wherein the pharmaceutically effective amount of a population of T cells is about $10^4$ to $10^9$ cells per kg body weight of the human patient.

8. The method of embodiment 2, wherein the pharmaceutically effective amount of a population of T cells is about $10^5$ to $10^6$ cells per kg body weight of the human patient.

9. The method of embodiment 2, wherein the pharmaceutically effective amount of a population of T cells is about $10^6$ to $10^7$ cells per kg body weight of the human patient.

10. The method of embodiment 2, wherein the pharmaceutically effective amount of a population of T cells is about $10^4$ to $10^5$ cells per kg body weight of the human patient.

11. The method of embodiment 2, wherein the pharmaceutically effective amount of a population of T cells is about $10^7$ to $10^8$ cells per kg body weight of the human patient.

12. The method of embodiment 2, wherein the pharmaceutically effective amount of a population of T cells is about $10^8$ to $10^9$ cells per kg body weight of the human patient.

13. The method of embodiment 2, wherein the CAR comprises the amino acid sequence of SEQ ID NO: 18, 19, or 20 and 21.

14. Use of a population of T cells expressing a CAR that binds an antigen associated with B cells for use in the treatment of autoimmune disease.

15. The use of claim 14, the autoimmune disease is Systemic Lupus Erythematosus (SLE), Rheumatoid Arthritis (RA), Type 1 Diabetes (T1D), Sjögren's syndrome, or Multiple Sclerosis (MS).

16. The use of embodiment 14 or 15, wherein the autoimmune disease is SLE.

17. The use of any one of embodiments 14-16, wherein the T cells include the amino acid sequence of any one of SEQ ID NO: 22-24 or 26.

18. The use of any one of embodiments 14-17, wherein the antigen is BAFF, APRIL, CD19, CD20, CD22, B cell receptor (BCR), B cell maturation antigen (BCMA) or CD79.

19. The use of any one of embodiments 14-18, wherein the antigen is CD19, CD20 or BCMA.

20. The use of any one of embodiments 14-19, wherein the pharmaceutically effective amount of the population of T cells is about $10^4$ to $10^9$ cells per kg body weight of the human patient.

21. The use of any one of embodiments 14-20, wherein the pharmaceutically effective amount of the population of T cells is about $10^5$ to $10^6$ cells per kg body weight of the human patient.

22. The use of any one of embodiments 14-21, wherein the pharmaceutically effective amount of the population of T cells is about $10^6$ to $10^7$ cells per kg body weight of the human patient.

23. The use of any one of embodiments 14-22, wherein the pharmaceutically effective amount of the population of T cells is about $10^4$ to $10^5$ cells per kg body weight of the human patient.

24. The use of any one of embodiments 14-23, wherein the pharmaceutically effective amount of the population of T cells is about $10^7$ to $10^8$ cells per kg body weight of the human patient.

25. The use of any one of embodiments 14-24, wherein the pharmaceutically effective amount of the population of T cells is about $10^8$ to $10^9$ cells per kg body weight of the human patient.

26. The use of any one of embodiments 14-25, wherein the CAR comprises the amino acid sequence of SEQ ID NO: 18, 19, or 20 and 21.

27. The use of any one of embodiments 14-26, wherein the use further includes measuring a level of: a urine protein, a serum anti-double-stranded DNA antibody, renal impairment, and/or damage to skin of the subject.

28. The use of any one of embodiments 14-27, wherein the level of the urine protein, the serum anti-double-stranded DNA antibody, the renal impairment, and/or the damage to the skin of the subject decreases.

Example 1

Expression of CAR on HEK293T & K562 Cells

Lentiviral vectors that encode a CD19 CAR were generated based on methods provided by Chimeric Receptors Containing CD137 Signal Transduction Domains Mediate Enhanced Survival of T Cells and Increased Antileukemic Efficacy In Vivo Molecular Therapy vol. 17 no. 8, 1453-1464 August 2009 incorporated herein by reference.

Figure 2:
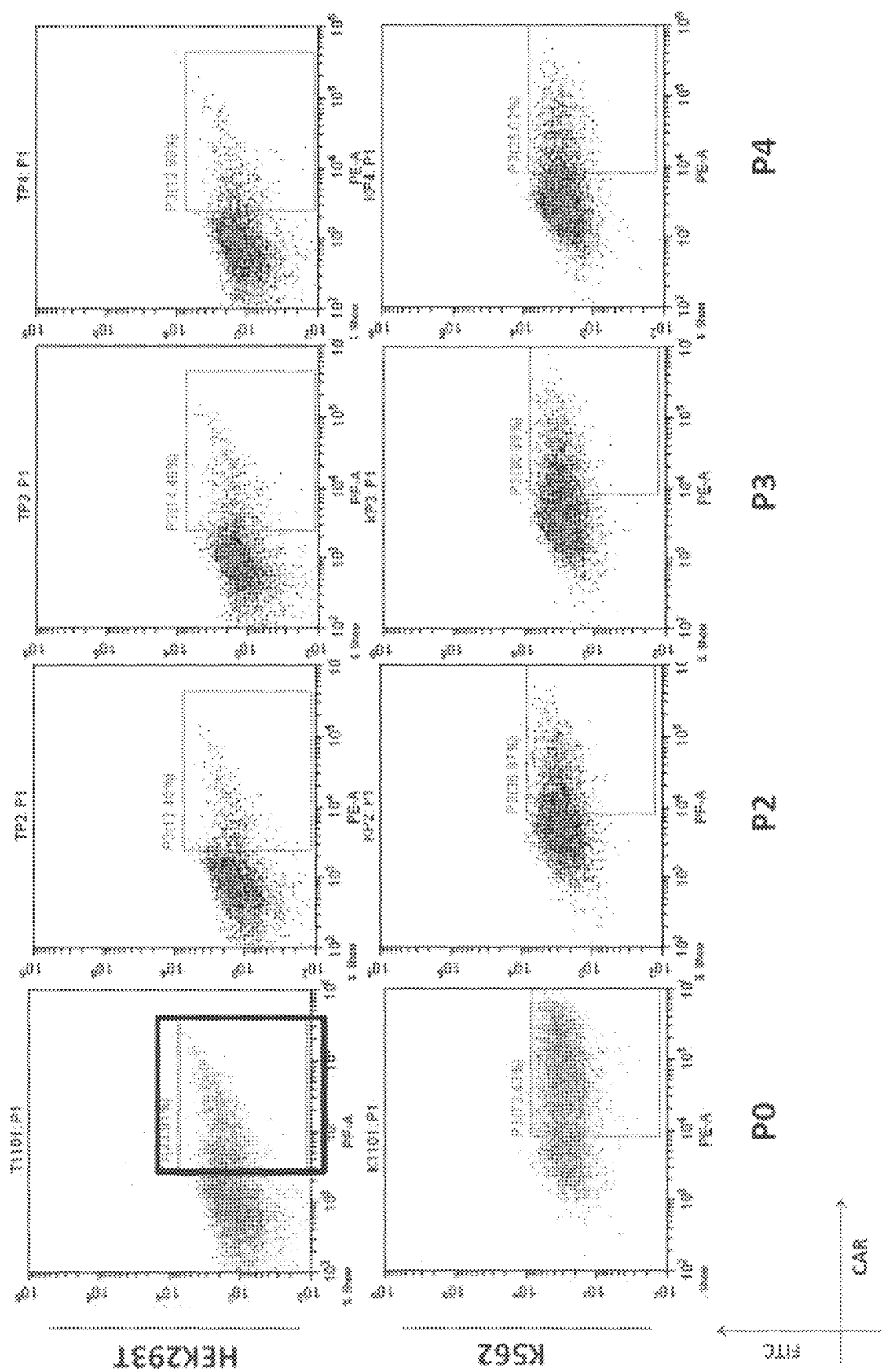
FIG. 2 shows expression of CAR on transduced 293T and K562 cells.

HEK293T & K562 cells were transduced with lentiviral vectors. Flow-cytometry acquisition was performed and analyzed to determine the expression of CAR in these cells. As shown in FIG. 2, both KECK293T and K562 cells expressed CARs (See Box in FIG. 2).

HEK293T and K562 cells were obtained from American Type Culture Collection (ATCC; Manassas, Va.). Techniques related to cell cultures, construction of lentiviral vectors, and flow cytometry may be found in Chimeric Receptors Containing CD137 Signal Transduction Domains Mediate Enhanced Survival of T Cells and Increased Anti-leukemic Efficacy In Vive Molecular Therapy vol. 17 no. 8, 1453-1464 August 2009 incorporated herein by reference, which is incorporated herein by reference.

Example 2

Expression of CAR on Primary T Cells and Cytotoxic T Lymphocyte Assay

Figure 3:
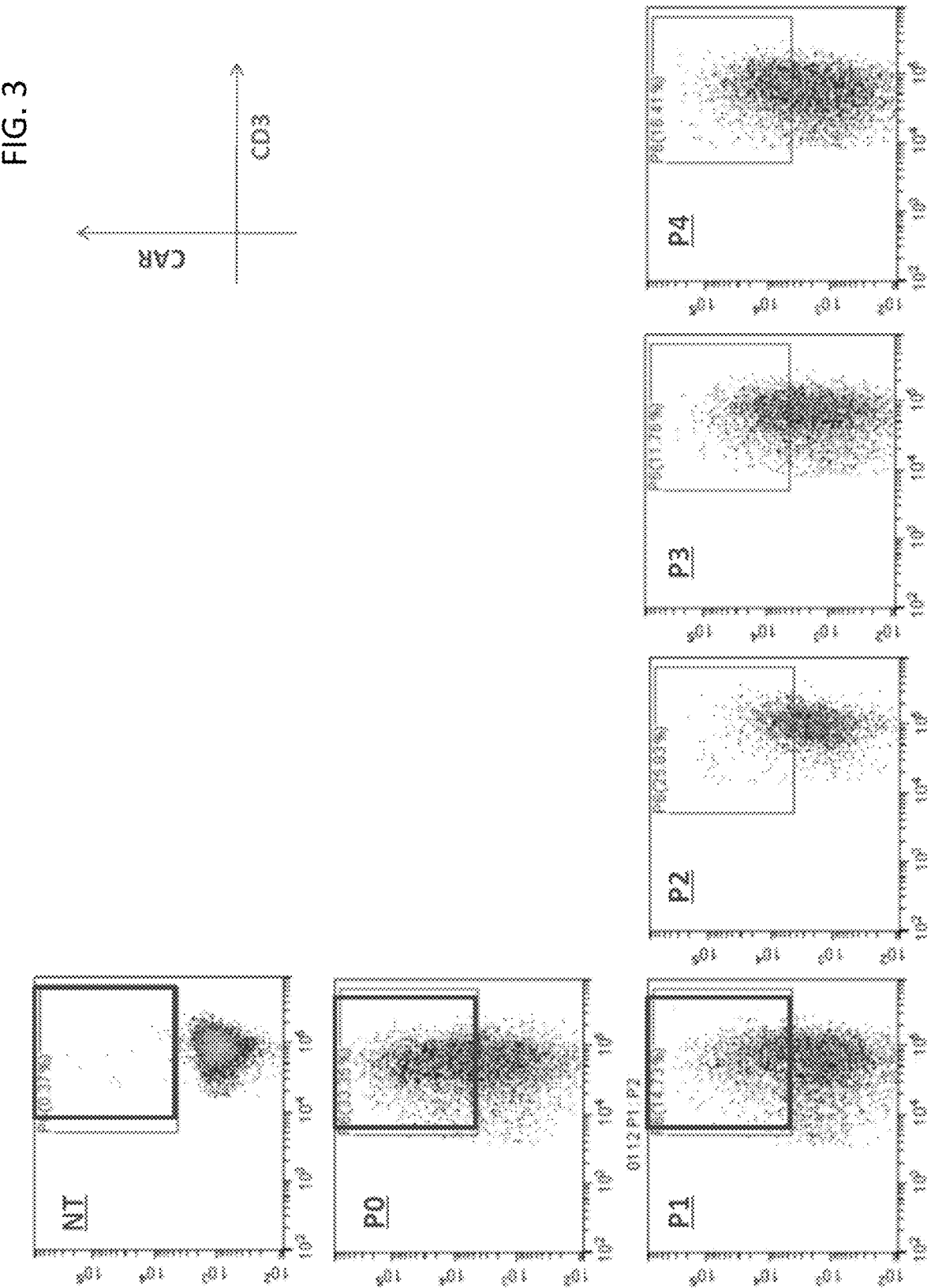
FIG. 3 shows expression of CAR on transduced primary T cells.

Primary T cells were obtained from patients. The obtained primary T cells were transduced with lentiviral vectors. Flow-cytometry acquisition was performed and analyzed to determine the expression of CAR and PD-1 in primary T cells. As shown in FIG. 3, primary T cells expressed CARs (See Box in FIG. 3).

Figure 5:
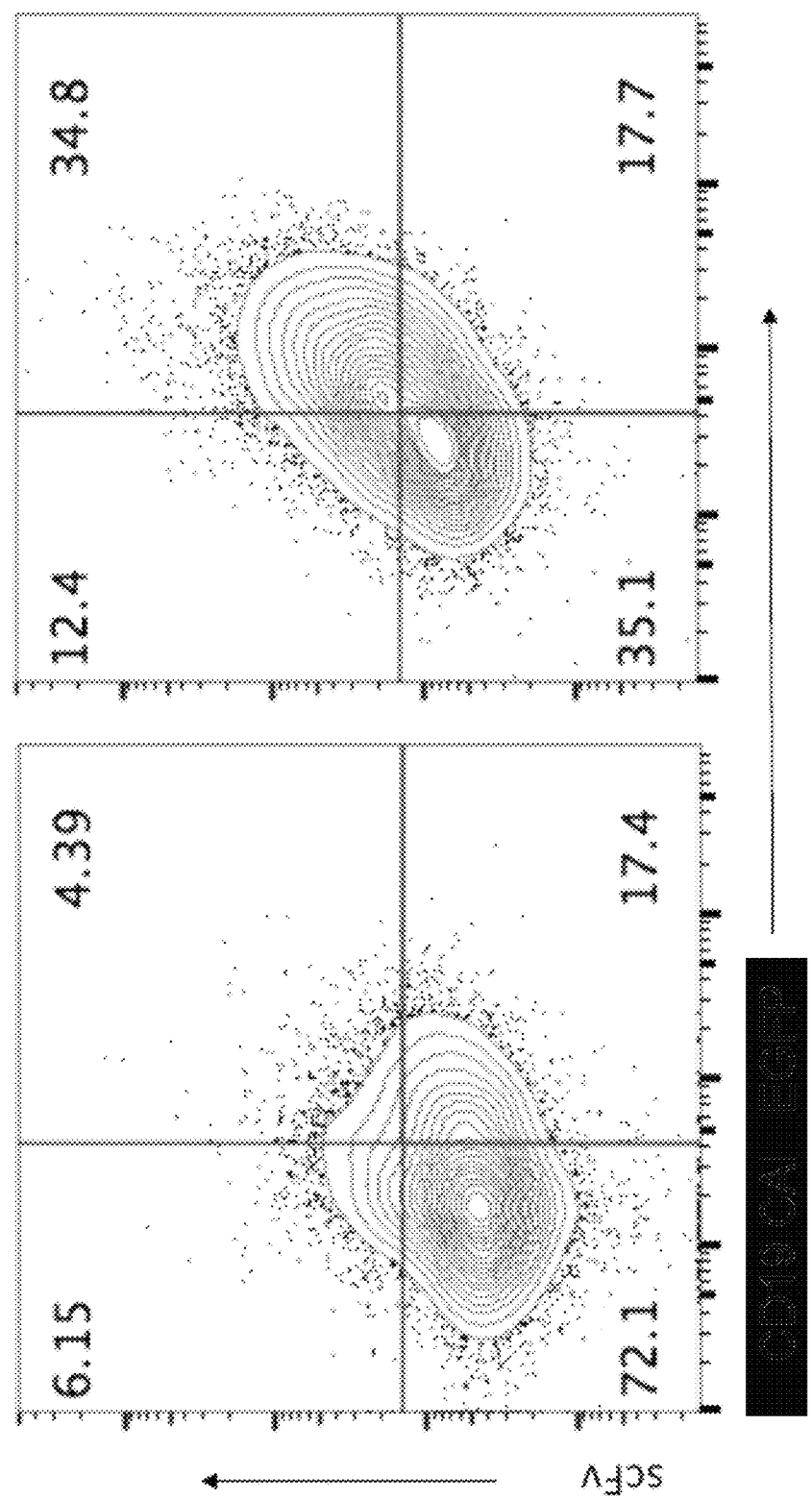
FIG. 5 shows the results of flow cytometry detection of scFv segment and EGFP fluorescently labeled double positive cells before and after transfection.

Techniques related to cell cultures, construction of lentiviral vectors, and flow cytometry may be found in Control of large, established tumor xenografts with genetically retargeted human T cells containing CD28 and CD137 domains (PNAS Mar. 3, 2009, vol. 106 no. 9, 3360-3365, which is incorporated herein by reference). FIG. 4 shows preparation of anti-mouse CD19CAR-T cells (CAR: SEQ ID NO: 22, and scFv: SEQ ID NO: 19). Firstly, a plasmid vector against mouse CD19 CAR was constructed, which consisted of anti-mouse CD19CAR gene and EGFP fluorescent marker gene. The two were ligated by IRES sequence, and the constructed vector was transfected into mouse T cells by lentivirus packaging. The transfected T cells can express an anti-mouse CD19CAR molecule on the cell membrane, and the structure includes an anti-murine CD19 scFv segment, a transmembrane hinge region, a murine CD137, and a murine CD3ζ fragment. FIG. 5 shows the results of flow detection of scFv segment and EGFP fluorescently labeled double positive cells before and after transfection. After performing flow cytometry, the scFv segment of CAR molecule and EGFP fluorescently labeled double positive cells, the ratio detected in non-transfected cells was 4.39% (background), and the proportion of double positive cells in the cells increased to 34.8 after transfection. This indicates that anti-mouse CD19CAR-T cells have been successfully prepared.

In this assay, the cytotoxicity on target cells (i.e., K562-CD19) is measured by comparing survival of target cells culturing with effector cells (i.e., transduced T cells) relative to the survival of target cells culturing with negative control cells (i.e., non-transduced T cells). Target cells and effector cells or negative control cells were cultured for about 24 hours with a number ratio between the target cells and effector cells or negative control cells being about 10:1. Survival rates of target cells and IFN-gamma production of transduced T cells and non-transduced T cells were measured. Transduced T cells containing nucleic acid sequences encoding CAR are capable of releasing IFN-gamma and killing CD19 cells. All error bars are representative of standard deviation.

Techniques related to cell cultures and construction of cytotoxic T lymphocyte assay may be found in Control of large, established tumor xenografts with genetically retargeted human T cells containing CD28 and CD137 domains (PNAS Mar. 3, 2009, vol. 106 no. 9, 3360-3365, which is incorporated herein by reference).

Figure 6:
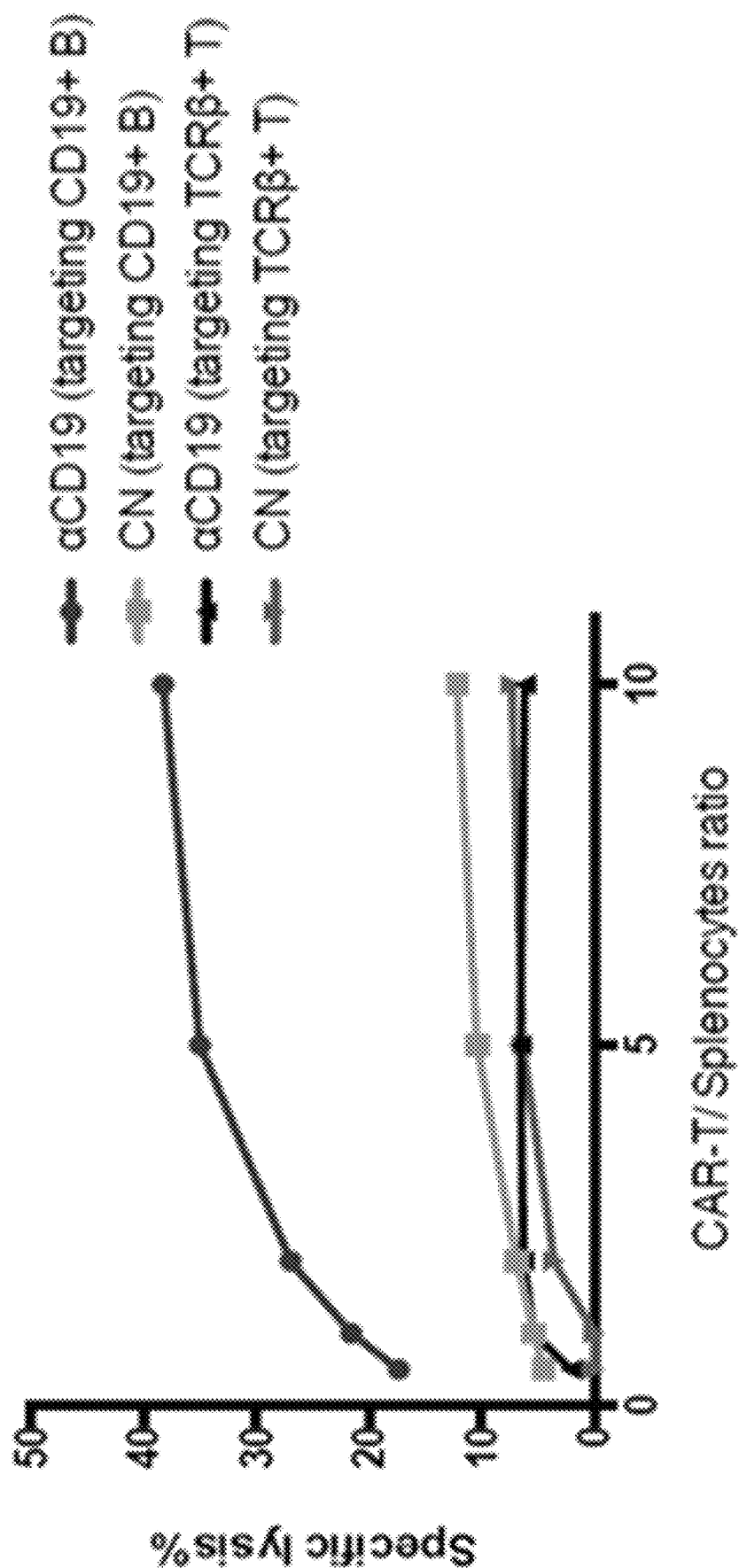
FIG. 6 shows specific killing of cells under in vitro co-culture conditions.

FIG. 6 shows specific killing of cells under in vitro co-culture conditions. The prepared anti-mouse CD19CAR-T cells were co-cultured with spleen cells containing a large number of B cells in vitro, and the specific killing of B cells by T cells was detected by isotope labeling technique (FIG. 6 Top line). The results of the other three control groups showed that the anti-mouse CD19 CAR-T cells had a significant killing effect on B cells.

Example 3

Treating SLE Disease Model Mice Using CD19 CAR T Cells

Figure 7:
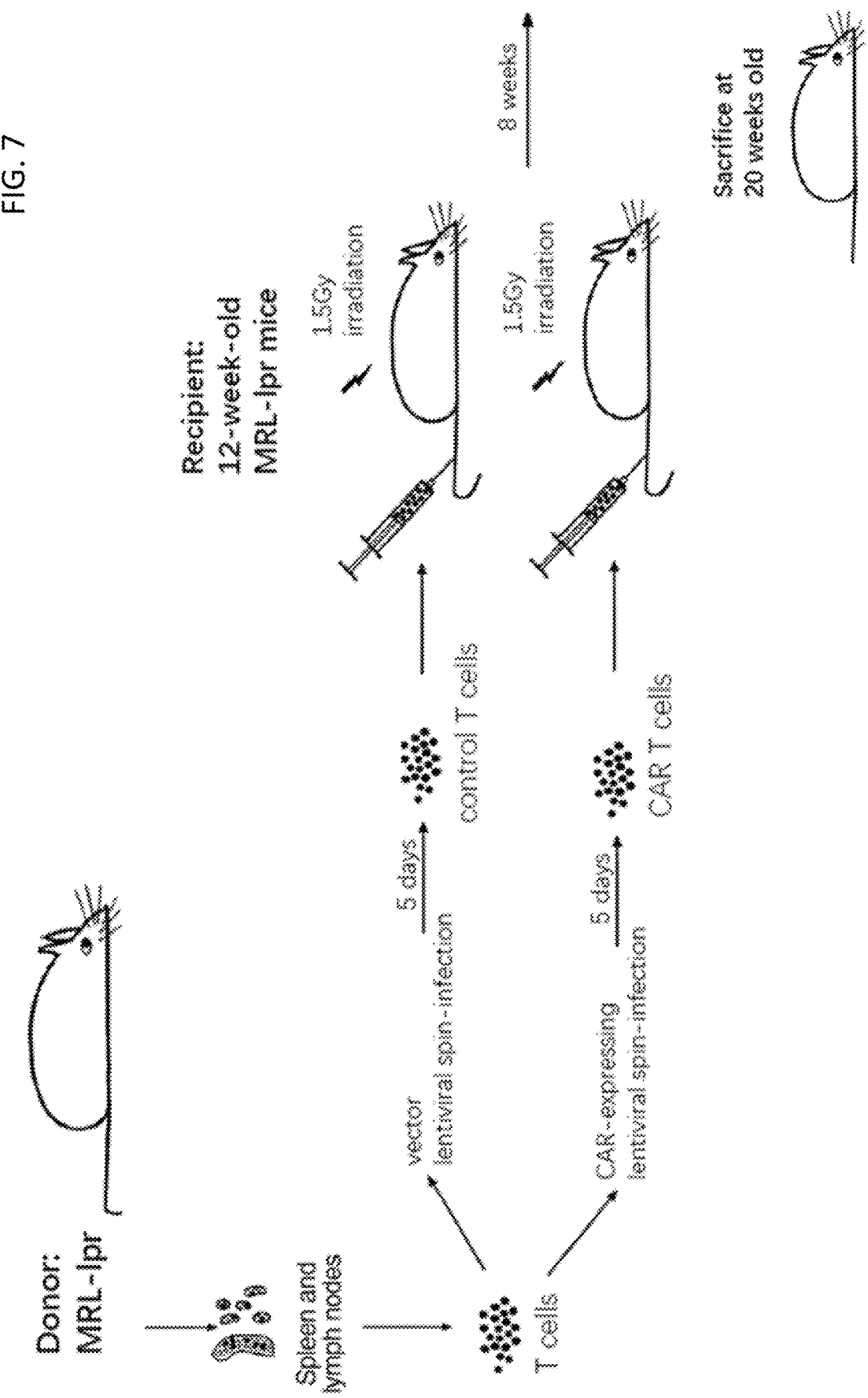
FIG. 7 illustrates anti-mouse CD19 CAR-T reinfusion treatment of SLE disease model mice experimental procedure.

FIG. 7 illustrates the anti-mouse CD19 CAR T reinfusion treatment of SLE disease model mice experimental procedure. The following animal experiments were designed. The spleen and lymph nodes of MRL-lpr mice (obtained from normal B6 mice and other strains of mice) were obtained, and the isolated T cell fraction was used to prepare anti-mouse CD19 CAR T cells (CAR: SEQ ID NO: 22, and scFv: SEQ ID NO: 19), and the other part was transfected with lentivirus. The plasmid vector was used as the control group. After 12 weeks, the MRL-lpr mice became the SLE disease model mice. After 1.5 Gy irradiation, the prepared anti-mouse CD19 CAR T cells and control T cells were observed. Experimental mice were sacrificed 8 weeks later.

FIG. 8 shows serum characterization of 12-week-old SLE disease model mice and normal B6 mice. Sera from 12-week-old SLE disease model mice and normal B6 mice were used to detect serum urinary nitrogen (BUN) content and anti-dsDNA antibody content in serum, and BUN content in serum of SLE disease model mice. The anti-dsDNA antibody content was significantly higher than that of normal mice, indicating that the SLE disease mice were successfully modeled.

Figure 9:
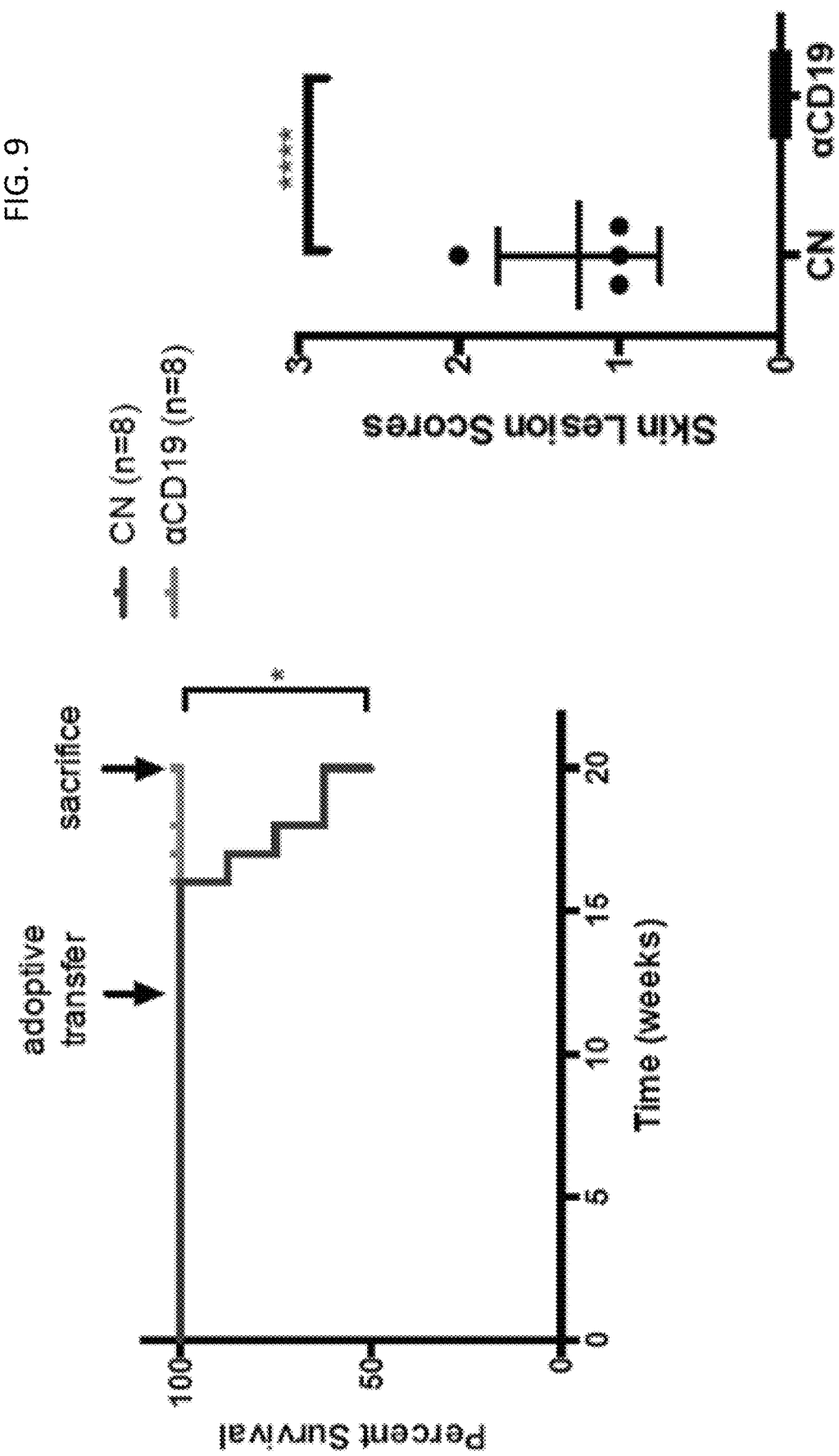
FIG. 9 shows survival status and skin damage of SLE disease model mice.

FIG. 9 show survival status and skin damage of SLE disease model mice. SLE disease model mice died after 16 weeks of T cells in the control group, and 50% of the mice in the control group died at 20 weeks. The skin of the mice showed different degrees of damage. The skin disorder included alopecia and progressed to skin lesions and scarring. In the group using anti-mouse CD19CAR-T cells, the mice in the experimental group all survived at 20 weeks, and no obvious damage was observed in the skin of the mice. It was shown that anti-mouse CD19CAR-T cells have a significant therapeutic effect on SLE disease model mice.

FIG. 10 shows the renal function damage of SLE disease model mice after treatment in the control group and the experimental group. After 20 weeks, the experimental mice were sacrificed. Biochemical indicators and pathological sections were observed. The SLE disease model mice that were transfused with anti-mouse CD19CAR-T cells showed anti-double-stranded DNA in urine protein and serum compared with the control group. The antibody content was down-regulated, indicating that the renal function damage of the experimental group was relieved. Pathological section staining showed that compared with normal B6 mice and anti-mouse CD19CAR-T cells, the control group showed obvious kidney damage, and the red arrow was glomerular destruction, blue. The arrow is the infiltration of lymphocytes, and the black arrow is the crescent of the epithelial cells of the glomerular wall.

Figure 11:
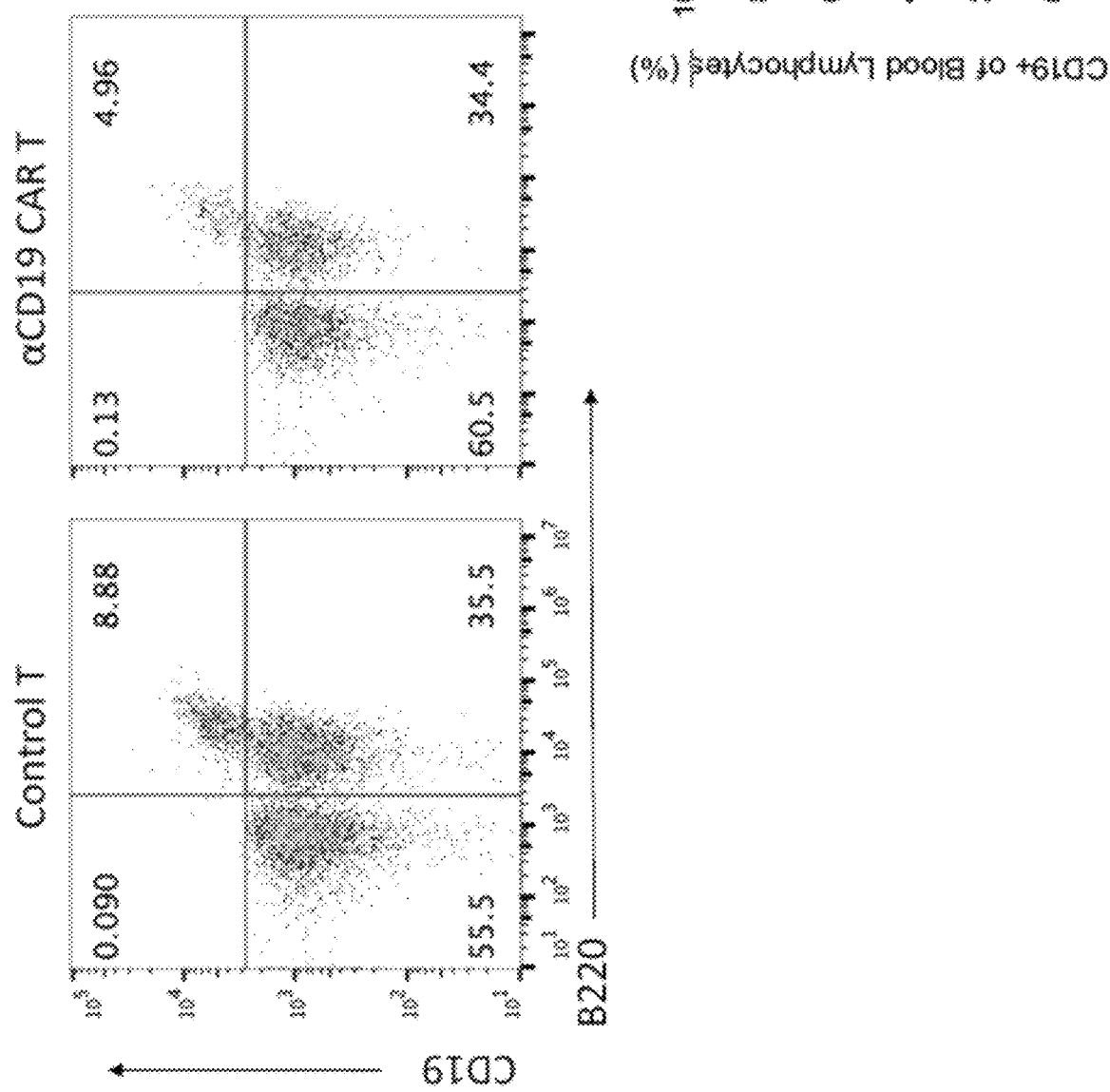
FIG. 11 shows the proportion of CD19+ cells in the blood of SLE disease model mice after one week of anti-mouse CD19 CAR-T cells treatment.

FIG. 11 shows the proportion of CD19+ cells in the blood of SLE disease model mice after one week of anti-mouse CD19 CAR-T cells treatment. After one week of treatment with anti-mouse CD19 CAR-T cells, SLE disease model mice showed a significant decrease in the proportion of CD19 and B220 double positive B cells in the blood by flow cytometry.

Figure 12:
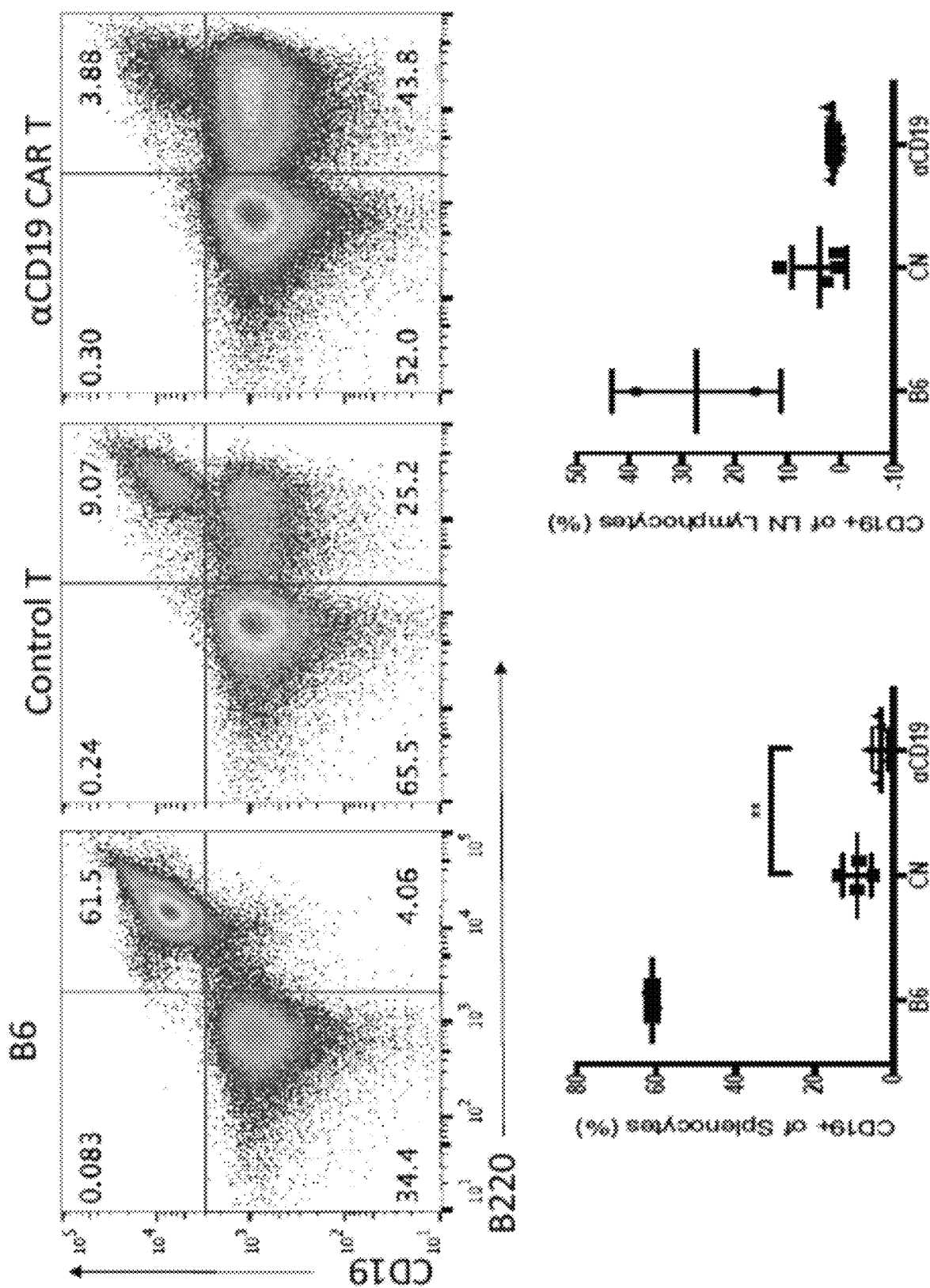
FIG. 12 shows the proportion of CD19+ cells in the spleen and lymph nodes of normal B6 mice and SLE disease model mice at 20 weeks of age.

FIG. 12 shows the proportion of CD19+ cells in the spleen and lymph nodes of normal B6 mice and SLE disease model mice at 20 weeks of age. Normal B6 mice and SLE disease model mice were subjected to flow cytometry on lymphocytes in spleen and lymph nodes at 20 weeks. The number of CD19+ cells in normal developing B6 mice was at a high level, and the control mice developed CD19+ cells due to SLE. Abnormally, the number of cells decreased significantly, and the mice in the experimental group treated with anti-mouse CD19 CAR-T cells further reduced the number of CD19+ cells.

Figure 13:
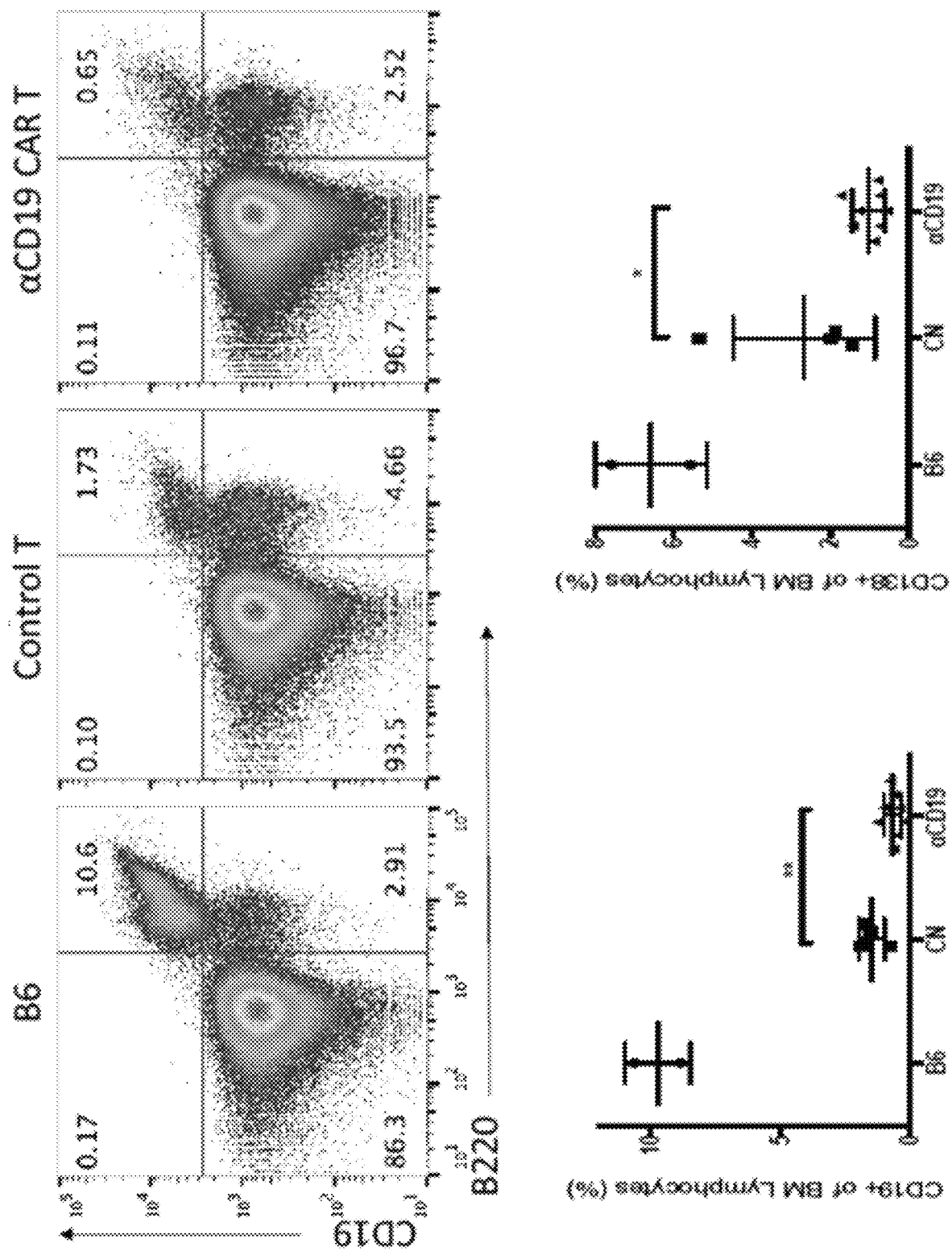
FIG. 13 shows the proportion of CD19+ cells and CD138+ cells in the bone marrow of normal B6 mice and SLE disease model mice at 20 weeks of age.

FIG. 13 shows the proportion of CD19+ cells and CD138+ cells in the bone marrow of normal B6 mice and SLE disease model mice at 20 weeks of age. Normal B6 mice and SLE disease model mice were used to detect the ratio of CD19+ cells and CD138+ cells (plasma cells) in bone marrow blood lymphocytes at 20 weeks. The number of normal developing B6 mice CD19+ cells and CD138+ cells was at a high level. In the control group, the number of CD19+ cells and CD138+ cells was significantly decreased by SLE, and the mice in the experimental group treated with anti-mouse CD19 CAR-T cells exhibited further reduced number of CD19+ cells and CD138+ cells.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

| Seq IDS | Identifier |
|---|---|
| 1 | SP |
| 2 | Linker |
| 3 | 4-1BB |
| 4 | CD3-zeta |
| 5 | WT CD3-zeta-aa |
| 6 | Group B// Hinge & TM domain |
| 7 | Group A// Hinge & TM domain |
| 8 | Group D // Hinge & TM domain |
| 9 | Group C // Hinge & TM domain |
| 10 | Group D // Hinge domain |
| 11 | Group C // Hinge domain |
| 12 | Group B Hinge domain |
| 13 | Group A // Hinge domain |
| 14 | Group D // TM domain |
| 15 | Group C // TM domain |
| 16 | Group B // domain |
| 17 | Group A // domain |
| 18 | scFv Humanized CD19 |
| 19 | scFv CD19 |
| 20 | VH region of BCMA scFv |
| 21 | VL region of BCMA scFv |
| 22 | CD19 CAR |
| 23 | hCD19 CAR |
| 24 | BCMA CAR |
| 25 | Tall-1 is a ligand for BCMA and may also function to specifically recognize BCMA Extracellular sequence of TALL-1 |
| 26 | Tall-1-CAR |

What is claimed is:

1. A method for treating Systemic Lupus Erythematosus (SLE) in a subject, the method comprising:
    administering to the subject a pharmaceutically effective amount of a population of T cells expressing a chimeric antigen receptor (CAR) that binds an antigen associated with B cells, wherein the CAR comprises amino acid sequence SEQ ID NO: 18.

2. The method of claim 1, wherein the antigen is CD19.

3. The method of claim 1, wherein the T cells comprise amino acid sequence SEQ ID NO: 23.

4. The method of claim 3, wherein the subject is a human patient and wherein the pharmaceutically effective amount of the population of T cells is about $10^4$ to $10^9$ cells per kg body weight of the human patient.

5. The method of claim 3, wherein the subject is a human patient and wherein the pharmaceutically effective amount of the population of T cells is about $10^5$ to $10^6$ cells per kg body weight of the human patient.

6. The method of claim 3, wherein the subject is a human patient and wherein the pharmaceutically effective amount of the population of T cells is about $10^6$ to $10^7$ cells per kg body weight of the human patient.

7. The method of claim 3, wherein the subject is a human patient and wherein the pharmaceutically effective amount of the population of T cells is about $10^4$ to $10^5$ cells per kg body weight of the human patient.

8. The method of claim 3, wherein the subject is a human patient and wherein the pharmaceutically effective amount of the population of T cells is about $10^7$ to $10^8$ cells per kg body weight of the human patient.

9. The method of claim 3, wherein the subject is a human patient and wherein the pharmaceutically effective amount of the population of T cells is about $10^8$ to $10^9$ cells per kg body weight of the human patient.

10. The method of claim 1, wherein the method further comprises measuring a level of: a urine protein, a serum anti-double-stranded DNA antibody, renal impairment, and/or damage to skin of the subject.

11. The method of claim 10, wherein the level of the urine protein, the serum anti-double-stranded DNA antibody, the renal impairment, and/or the damage to the skin of the subject decreases, as compared to a control subject.

\* \* \* \* \*

SEQUENCE LISTING

```
<160> NUMBER OF SEQ ID NOS: 27

<210> SEQ ID NO 1
<211> LENGTH: 21
<212> TYPE: PRT
<213> ORGANISM: Artificial Sequence
<220> FEATURE:
<223> OTHER INFORMATION: Synthesized

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 15
<212> TYPE: PRT
<213> ORGANISM: Artificial Sequence
<220> FEATURE:
<223> OTHER INFORMATION: Synthesized

<400> SEQUENCE: 2

Gly Gly Gly Gly Ser Gly Gly Gly Ser Gly Gly Gly Gly Ser
1               5                   10                  15

<210> SEQ ID NO 3
<211> LENGTH: 42
<212> TYPE: PRT
<213> ORGANISM: Homo sapiens

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 4
<211> LENGTH: 112
```

```
<212> TYPE: PRT
<213> ORGANISM: Homo sapiens

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 5
<211> LENGTH: 339
<212> TYPE: DNA
<213> ORGANISM: Artificial Sequence
<220> FEATURE:
<223> OTHER INFORMATION: Synthesized

<400> SEQUENCE: 5
agagtgaagt tcagcaggag cgcagacgcc cccgcgtacc agcagggcca gaaccagctc       60
tataacgagc tcaatctagg acgaagagag gagtacgatg ttttggacaa gaggcgtggc      120
cgggaccctg agatggggggg aaagccgaga aggaagaacc ctcaggaagg cctgtacaat     180
gaactgcaga aagataagat ggcggaggcc tacagtgaga ttgggatgaa aggcgagcgc      240 cggagggggca aggggcacga tggcctttac cagggtctca gtacagccac caaggacacc    300
tacgacgccc ttcacatgca ggccctgccc cctcgctaa                             339

<210> SEQ ID NO 6
<211> LENGTH: 66
<212> TYPE: PRT
<213> ORGANISM: Artificial Sequence
<220> FEATURE:
<223> OTHER INFORMATION: Synthesized

<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr
65

<210> SEQ ID NO 7
<211> LENGTH: 69
<212> TYPE: PRT
<213> ORGANISM: Artificial Sequence
<220> FEATURE:
```

<223> OTHER INFORMATION: Synthesized

<400> SEQUENCE: 7

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 8
<211> LENGTH: 72
<212> TYPE: PRT
<213> ORGANISM: Artificial Sequence
<220> FEATURE:
<223> OTHER INFORMATION: Synthesized

<400> SEQUENCE: 8

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr Leu Tyr Cys
65                  70

<210> SEQ ID NO 9
<211> LENGTH: 69
<212> TYPE: PRT
<213> ORGANISM: Artificial Sequence
<220> FEATURE:
<223> OTHER INFORMATION: Synthesized

<400> SEQUENCE: 9

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65

<210> SEQ ID NO 10
<211> LENGTH: 50
<212> TYPE: PRT
<213> ORGANISM: Artificial Sequence
<220> FEATURE:
<223> OTHER INFORMATION: Synthesized

<400> SEQUENCE: 10

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr
    50

<210> SEQ ID NO 11
<211> LENGTH: 50
<212> TYPE: PRT
<213> ORGANISM: Artificial Sequence
<220> FEATURE:
<223> OTHER INFORMATION: Synthesized

<400> SEQUENCE: 11

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr
    50

<210> SEQ ID NO 12
<211> LENGTH: 47
<212> TYPE: PRT
<213> ORGANISM: Artificial Sequence
<220> FEATURE:
<223> OTHER INFORMATION: Synthesized

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 13
<211> LENGTH: 47
<212> TYPE: PRT
<213> ORGANISM: Artificial Sequence
<220> FEATURE:
<223> OTHER INFORMATION: Synthesized

<400> SEQUENCE: 13

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 14
<211> LENGTH: 22
<212> TYPE: PRT
<213> ORGANISM: Artificial Sequence
<220> FEATURE:
<223> OTHER INFORMATION: Synthesized
```

-continued

<400> SEQUENCE: 14

Ile Trp Ala Pro Leu Ala Gly Thr Cys Gly Val Leu Leu Ser Leu
1               5                   10                  15

Val Ile Thr Leu Tyr Cys
            20

<210> SEQ ID NO 15
<211> LENGTH: 19
<212> TYPE: PRT
<213> ORGANISM: Artificial Sequence
<220> FEATURE:
<223> OTHER INFORMATION: Synthesized

<400> SEQUENCE: 15

Ile Trp Ala Pro Leu Ala Gly Thr Cys Gly Val Leu Leu Ser Leu
1               5                   10                  15

Val Ile Thr

<210> SEQ ID NO 16
<211> LENGTH: 19
<212> TYPE: PRT
<213> ORGANISM: Artificial Sequence
<220> FEATURE:
<223> OTHER INFORMATION: Synthesized

<400> SEQUENCE: 16

Ile Trp Ala Pro Leu Ala Gly Thr Cys Gly Val Leu Leu Ser Leu
1               5                   10                  15

Val Ile Thr

<210> SEQ ID NO 17
<211> LENGTH: 22
<212> TYPE: PRT
<213> ORGANISM: Artificial Sequence
<220> FEATURE:
<223> OTHER INFORMATION: Synthesized

<400> SEQUENCE: 17

Ile Trp Ala Pro Leu Ala Gly Thr Cys Gly Val Leu Leu Ser Leu
1               5                   10                  15

Val Ile Thr Leu Tyr Cys
            20

<210> SEQ ID NO 18
<211> LENGTH: 242
<212> TYPE: PRT
<213> ORGANISM: Artificial Sequence
<220> FEATURE:
<223> OTHER INFORMATION: Synthesized

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
            180                 185                 190

Arg Asp Asn Ala Lys Asn Ser Leu Tyr Leu Gln Met Asn Ser Leu Arg
        195                 200                 205

Ala Glu Asp Thr Ala Val Tyr Tyr Cys Ala Lys His Tyr Tyr Tyr Gly
210                 215                 220

Gly Ser Tyr Ala Met Asp Tyr Trp Gly Gln Gly Thr Leu Val Thr Val
225                 230                 235                 240

Ser Ser

<210> SEQ ID NO 19
<211> LENGTH: 242
<212> TYPE: PRT
<213> ORGANISM: Artificial Sequence
<220> FEATURE:
<223> OTHER INFORMATION: Synthesized

<400> SEQUENCE: 19

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190
```

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
        210                 215                 220

Gly Ser Tyr Ala Met Asp Tyr Trp Gly Gln Gly Thr Ser Val Thr Val
225                 230                 235                 240

Ser Ser

<210> SEQ ID NO 20
<211> LENGTH: 115
<212> TYPE: PRT
<213> ORGANISM: Artificial Sequence
<220> FEATURE:
<223> OTHER INFORMATION: Synthesized

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Leu Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
        115

<210> SEQ ID NO 21
<211> LENGTH: 108
<212> TYPE: PRT
<213> ORGANISM: Artificial Sequence
<220> FEATURE:
<223> OTHER INFORMATION: Synthesized

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Gly Gly Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Ser Trp Pro
                85                  90                  95

Leu Thr Phe Gly Gln Gly Thr Lys Val Glu Ile Lys
            100                 105

<210> SEQ ID NO 22
<211> LENGTH: 486

<212> TYPE: PRT
<213> ORGANISM: Artificial Sequence
<220> FEATURE:
<223> OTHER INFORMATION: Synthesized

<400> SEQUENCE: 22

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380
```

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 23
<211> LENGTH: 486
<212> TYPE: PRT
<213> ORGANISM: Artificial Sequence
<220> FEATURE:
<223> OTHER INFORMATION: Synthesized

<400> SEQUENCE: 23

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Lys Ala
    50                  55                  60

Pro Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Gly
            100                 105                 110

Asn Thr Leu Pro Tyr Thr Phe Gly Gln Gly Thr Lys Val Glu Ile Lys
        115                 120                 125

Gly Gly Gly Gly Ser Gly Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Val Ser Leu Pro Asp Tyr Gly
                165                 170                 175

Val Ser Trp Val Arg Gln Ala Pro Gly Lys Gly Leu Glu Trp Val Ser
            180                 185                 190

Val Ile Trp Gly Ser Glu Thr Thr Tyr Tyr Asn Ser Ala Leu Lys Ser
        195                 200                 205

Arg Phe Thr Ile Ser Arg Asp Asn Ala Lys Asn Ser Leu Tyr Leu Gln
    210                 215                 220

Met Asn Ser Leu Arg Ala Glu Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

```
Thr Leu Val Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Arg
                485

<210> SEQ ID NO 24
<211> LENGTH: 483
<212> TYPE: PRT
<213> ORGANISM: Artificial Sequence
<220> FEATURE:
<223> OTHER INFORMATION: Synthesized

<400> SEQUENCE: 24

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Gly Phe
        35                  40                  45

Ala Leu Ser Asn His Gly Met Ser Trp Val Arg Arg Ala Pro Gly Lys
    50                  55                  60

Gly Leu Glu Trp Val Ser Gly Ile Val Tyr Ser Gly Ser Thr Tyr Tyr
65                  70                  75                  80

Ala Ala Ser Val Lys Gly Arg Phe Thr Ile Ser Arg Asp Asn Ser Arg
                85                  90                  95

Asn Thr Leu Tyr Leu Gln Met Asn Ser Leu Arg Pro Glu Asp Thr Ala
            100                 105                 110

Ile Tyr Tyr Cys Ser Ala His Gly Gly Glu Ser Asp Val Trp Gly Gln
        115                 120                 125
```

Gly Thr Thr Val Thr Val Ser Ser Ala Ser Gly Gly Gly Ser Gly
    130             135             140

Gly Arg Ala Ser Gly Gly Gly Ser Asp Ile Gln Leu Thr Gln Ser
145             150             155             160

Pro Ser Ser Leu Ser Ala Ser Val Gly Asp Arg Val Thr Ile Thr Cys
            165             170             175

Arg Ala Ser Gln Ser Ile Ser Ser Tyr Leu Asn Trp Tyr Gln Gln Lys
        180             185             190

Pro Gly Lys Ala Pro Lys Leu Leu Ile Tyr Ala Ala Ser Ser Leu Gln
    195             200             205

Ser Gly Val Pro Ser Arg Phe Ser Gly Ser Gly Ser Gly Thr Asp Phe
210             215             220

Thr Leu Thr Ile Ser Ser Leu Gln Pro Glu Asp Phe Ala Thr Tyr Tyr
225             230             235             240

Cys Gln Gln Ser Tyr Ser Thr Pro Tyr Thr Phe Gly Gln Gly Thr Lys
            245             250             255

Val Glu Ile Lys Thr Thr Thr Pro Ala Pro Arg Pro Pro Thr Pro Ala
        260             265             270

Pro Thr Ile Ala Ser Gln Pro Leu Ser Leu Arg Pro Glu Ala Cys Arg
    275             280             285

Pro Ala Ala Gly Gly Ala Val His Thr Arg Gly Leu Asp Phe Ala Cys
290             295             300

Asp Ile Tyr Ile Trp Ala Pro Leu Ala Gly Thr Cys Gly Val Leu Leu
305             310             315             320

Leu Ser Leu Val Ile Thr Leu Tyr Cys Lys Arg Gly Arg Lys Lys Leu
            325             330             335

Leu Tyr Ile Phe Lys Gln Pro Phe Met Arg Pro Val Gln Thr Thr Gln
        340             345             350

Glu Glu Asp Gly Cys Ser Cys Arg Phe Pro Glu Glu Glu Gly Gly
    355             360             365

Cys Glu Leu Arg Val Lys Phe Ser Arg Ser Ala Asp Ala Pro Ala Tyr
370             375             380

Gln Gln Gly Gln Asn Gln Leu Tyr Asn Glu Leu Asn Leu Gly Arg Arg
385             390             395             400

Glu Glu Tyr Asp Val Leu Asp Lys Arg Gly Arg Asp Pro Glu Met
            405             410             415

Gly Gly Lys Pro Arg Arg Lys Asn Pro Gln Glu Gly Leu Tyr Asn Glu
        420             425             430

Leu Gln Lys Asp Lys Met Ala Glu Ala Tyr Ser Glu Ile Gly Met Lys
    435             440             445

Gly Glu Arg Arg Arg Gly Lys Gly His Asp Gly Leu Tyr Gln Gly Leu
450             455             460

Ser Thr Ala Thr Lys Asp Thr Tyr Asp Ala Leu His Met Gln Ala Leu
465             470             475             480

Pro Pro Arg

<210> SEQ ID NO 25
<211> LENGTH: 218
<212> TYPE: PRT
<213> ORGANISM: Artificial Sequence
<220> FEATURE:
<223> OTHER INFORMATION: Synthesized

<400> SEQUENCE: 25

Gln Val Ala Ala Leu Gln Gly Asp Leu Ala Ser Leu Arg Ala Glu Leu

```
1               5                   10                  15
Gln Gly His His Ala Glu Lys Leu Pro Ala Gly Ala Pro Lys
                20                  25                  30
Ala Gly Leu Glu Glu Ala Pro Ala Val Thr Ala Gly Leu Lys Ile Phe
                35                  40                  45
Glu Pro Pro Ala Pro Gly Glu Gly Asn Ser Ser Gln Asn Ser Arg Asn
                50                  55                  60
Lys Arg Ala Val Gln Gly Pro Glu Glu Thr Val Thr Gln Asp Cys Leu
65                                  70                  75                  80
Gln Leu Ile Ala Asp Ser Glu Thr Pro Thr Ile Gln Lys Gly Ser Tyr
                        85                  90                  95
Thr Phe Val Pro Trp Leu Leu Ser Phe Lys Arg Gly Ser Ala Leu Glu
                        100                 105                 110
Glu Lys Glu Asn Lys Ile Leu Val Lys Glu Thr Gly Tyr Phe Phe Ile
                        115                 120                 125
Tyr Gly Gln Val Leu Tyr Thr Asp Lys Thr Tyr Ala Met Gly His Leu
                130                 135                 140
Ile Gln Arg Lys Lys Val His Val Phe Gly Asp Glu Leu Ser Leu Val
145                         150                 155                 160
Thr Leu Phe Arg Cys Ile Gln Asn Met Pro Glu Thr Leu Pro Asn Asn
                        165                 170                 175
Ser Cys Tyr Ser Ala Gly Ile Ala Lys Leu Glu Glu Gly Asp Glu Leu
                        180                 185                 190
Gln Leu Ala Ile Pro Arg Glu Asn Ala Gln Ile Ser Leu Asp Gly Asp
                        195                 200                 205
Val Thr Phe Phe Gly Ala Leu Lys Leu Leu
                        210                 215

<210> SEQ ID NO 26
<211> LENGTH: 462
<212> TYPE: PRT
<213> ORGANISM: Artificial Sequence
<220> FEATURE:
<223> OTHER INFORMATION: Synthesized

<400> SEQUENCE: 26

Met Ala Leu Pro Val Thr Ala Leu Leu Leu Pro Leu Ala Leu Leu Leu
1               5                   10                  15
His Ala Ala Arg Pro Gln Val Ala Leu Gln Gly Asp Leu Ala Ser
                20                  25                  30
Leu Arg Ala Glu Leu Gln Gly His His Ala Glu Lys Leu Pro Ala Gly
                35                  40                  45
Ala Gly Ala Pro Lys Ala Gly Leu Glu Glu Ala Pro Ala Val Thr Ala
                50                  55                  60
Gly Leu Lys Ile Phe Glu Pro Pro Ala Pro Gly Glu Gly Asn Ser Ser
65                          70                  75                  80
Gln Asn Ser Arg Asn Lys Arg Ala Val Gln Gly Pro Glu Glu Thr Val
                        85                  90                  95
Thr Gln Asp Cys Leu Gln Leu Ile Ala Asp Ser Glu Thr Pro Thr Ile
                        100                 105                 110
Gln Lys Gly Ser Tyr Thr Phe Val Pro Trp Leu Leu Ser Phe Lys Arg
                115                 120                 125
Gly Ser Ala Leu Glu Glu Lys Glu Asn Lys Ile Leu Val Lys Glu Thr
                130                 135                 140
Gly Tyr Phe Phe Ile Tyr Gly Gln Val Leu Tyr Thr Asp Lys Thr Tyr
```

```
            145                 150                 155                 160
        Ala Met Gly His Leu Ile Gln Arg Lys Lys Val His Val Phe Gly Asp
                        165                 170                 175
        Glu Leu Ser Leu Val Thr Leu Phe Arg Cys Ile Gln Asn Met Pro Glu
                        180                 185                 190
        Thr Leu Pro Asn Asn Ser Cys Tyr Ser Ala Gly Ile Ala Lys Leu Glu
                    195                 200                 205
        Glu Gly Asp Glu Leu Gln Leu Ala Ile Pro Arg Glu Asn Ala Gln Ile
                    210                 215                 220
        Ser Leu Asp Gly Asp Val Thr Phe Phe Gly Ala Leu Lys Leu Leu Thr
        225                 230                 235                 240
        Thr Thr Pro Ala Pro Arg Pro Pro Thr Pro Ala Pro Thr Ile Ala Ser
                        245                 250                 255
        Gln Pro Leu Ser Leu Arg Pro Glu Ala Cys Arg Pro Ala Ala Gly Gly
                        260                 265                 270
        Ala Val His Thr Arg Gly Leu Asp Phe Ala Cys Asp Ile Tyr Ile Trp
                        275                 280                 285
        Ala Pro Leu Ala Gly Thr Cys Gly Val Leu Leu Leu Ser Leu Val Ile
                    290                 295                 300
        Thr Leu Tyr Cys Lys Arg Gly Arg Lys Lys Leu Leu Tyr Ile Phe Lys
        305                 310                 315                 320
        Gln Pro Phe Met Arg Pro Val Gln Thr Thr Gln Glu Glu Asp Gly Cys
                        325                 330                 335
        Ser Cys Arg Phe Pro Glu Glu Glu Glu Gly Gly Cys Glu Leu Arg Val
                        340                 345                 350
        Lys Phe Ser Arg Ser Ala Asp Ala Pro Ala Tyr Gln Gln Gly Gln Asn
                        355                 360                 365
        Gln Leu Tyr Asn Glu Leu Asn Leu Gly Arg Arg Glu Glu Tyr Asp Val
                    370                 375                 380
        Leu Asp Lys Arg Arg Gly Arg Asp Pro Glu Met Gly Gly Lys Pro Arg
        385                 390                 395                 400
        Arg Lys Asn Pro Gln Glu Gly Leu Tyr Asn Glu Leu Gln Lys Asp Lys
                        405                 410                 415
        Met Ala Glu Ala Tyr Ser Glu Ile Gly Met Lys Gly Glu Arg Arg Arg
                        420                 425                 430
        Gly Lys Gly His Asp Gly Leu Tyr Gln Gly Leu Ser Thr Ala Thr Lys
                        435                 440                 445
        Asp Thr Tyr Asp Ala Leu His Met Gln Ala Leu Pro Pro Arg
                450                 455                 460

<210> SEQ ID NO 27
<211> LENGTH: 15
<212> TYPE: PRT
<213> ORGANISM: Artificial Sequence
<220> FEATURE:
<223> OTHER INFORMATION: Synthetsized

<400> SEQUENCE: 27

Gly Gly Gly Gly Ser Gly Gly Gly Gly Ser Gly Gly Gly Gly Ser
1               5                   10                  15
```